(12) United States Patent
Mann et al.

(10) Patent No.: US 11,291,161 B2
(45) Date of Patent: Apr. 5, 2022

(54) SYSTEMS AND METHODS FOR GROWING VEGETATION

(71) Applicant: BENNAMANN SERVICES LTD, Newquay (GB)

(72) Inventors: Christopher Mann, Cornwall (GB); Michael Bennett, Cornwall (GB); Derek William Kenneth Jenkins, Oxfordshire (GB); Thomas William Bradshaw, Oxon (GB); Matthew Charles Seabrook Heritage, Oxon (GB)

(73) Assignee: BENNAMANN SERVICES LTD, Newquay (GB)

( * ) Notice: Subject to any disclaimer, the term of this patent is extended or adjusted under 35 U.S.C. 154(b) by 638 days.

(21) Appl. No.: 15/998,748

(22) PCT Filed: Feb. 16, 2017

(86) PCT No.: PCT/IB2017/050854
§ 371 (c)(1),
(2) Date: Aug. 16, 2018

(87) PCT Pub. No.: WO2017/141178
PCT Pub. Date: Aug. 24, 2017

(65) Prior Publication Data
US 2020/0281132 A1    Sep. 10, 2020

Related U.S. Application Data

(60) Provisional application No. 62/295,893, filed on Feb. 16, 2016.

(51) Int. Cl.
*A01G 20/20* (2018.01)
*A01D 43/00* (2006.01)
(Continued)

(52) U.S. Cl.
CPC .............. *A01D 43/00* (2013.01); *A01G 3/00* (2013.01); *A01G 3/002* (2013.01); *A01G 7/045* (2013.01);
(Continued)

(58) Field of Classification Search
CPC ........ A01G 20/12; A01G 20/20; A01G 3/002; A01G 7/045; B63B 35/44;
(Continued)

(56) References Cited

U.S. PATENT DOCUMENTS

| 3,300,896 A | 1/1967 | Lunstroth |
| 3,425,158 A | 2/1969 | Kyle |

(Continued)

FOREIGN PATENT DOCUMENTS

| AU | 2003252206 A1 | 4/2005 |
| CN | 101314780 A | 12/2008 |

(Continued)

OTHER PUBLICATIONS

International Preliminary Report on Patentability and Written Opinion issued in corresponding International Application No. PCT/IB2017/050854, dated Aug. 21, 2018, 11 pages.
(Continued)

*Primary Examiner* — David W Berke-Schlessel
*Assistant Examiner* — Trent R Clarke
(74) *Attorney, Agent, or Firm* — Rothwell, Figg, Ernst & Manbeck, P.C.

(57) ABSTRACT

Systems and methods for growing vegetation are provided. The disclosed systems (100) and methods (1100, 1200) use rotating growth mats (102) and a cutting device (112). The rotating growth mats and cutting device can be coupled to an anaerobic digester (402) to generated methane gas using vegetation grown on the growth mats. The systems and
(Continued)

methods may further use C artificial light sources (108) and a nutrients delivery system (110) to assist growth.

11 Claims, 20 Drawing Sheets

(51) Int. Cl.
| | |
|---|---|
| *A01G 3/00* | (2006.01) |
| *A01G 7/04* | (2006.01) |
| *B63B 35/44* | (2006.01) |
| *C12M 1/00* | (2006.01) |
| *C12P 5/02* | (2006.01) |
| *C02F 11/04* | (2006.01) |
| *C12M 1/107* | (2006.01) |
| *C12M 1/33* | (2006.01) |
| *B02C 18/02* | (2006.01) |
| *A01G 20/12* | (2018.01) |

(52) U.S. Cl.
CPC ............ *A01G 20/12* (2018.02); *A01G 20/20* (2018.02); *B02C 18/02* (2013.01); *B63B 35/44* (2013.01); *C02F 11/04* (2013.01); *C12M 21/04* (2013.01); *C12M 43/04* (2013.01); *C12M 43/08* (2013.01); *C12M 45/02* (2013.01); *C12P 5/023* (2013.01); *B63B 2035/4493* (2013.01)

(58) Field of Classification Search
CPC ........... B63B 2035/4493; C12M 21/04; C12M 43/04; C12M 45/02; C12P 5/023
See application file for complete search history.

(56) References Cited

U.S. PATENT DOCUMENTS

| | | | |
|---|---|---|---|
| 4,950,444 A | | 8/1990 | Deboufie et al. |
| 2012/0308989 A1 | | 12/2012 | Barclay et al. |
| 2013/0247451 A1* | | 9/2013 | Vanhercke ............. C10L 1/026 |
| | | | 44/388 |

FOREIGN PATENT DOCUMENTS

| | | |
|---|---|---|
| CN | 101392019 A | 3/2009 |
| DE | 1782764 A1 | 8/1972 |
| DE | 3817289 A1 | 11/1989 |
| WO | 9615661 A1 | 5/1996 |

OTHER PUBLICATIONS

International Search Report and Written Opinion dated Jul. 21, 2017, in International Application No. PCT/IB2017/050054, 10 pages.
First Chinese Office Action issued in corresponding Chinese Application No. 2017800117905, dated Mar. 23, 2020, 24 pages.

* cited by examiner

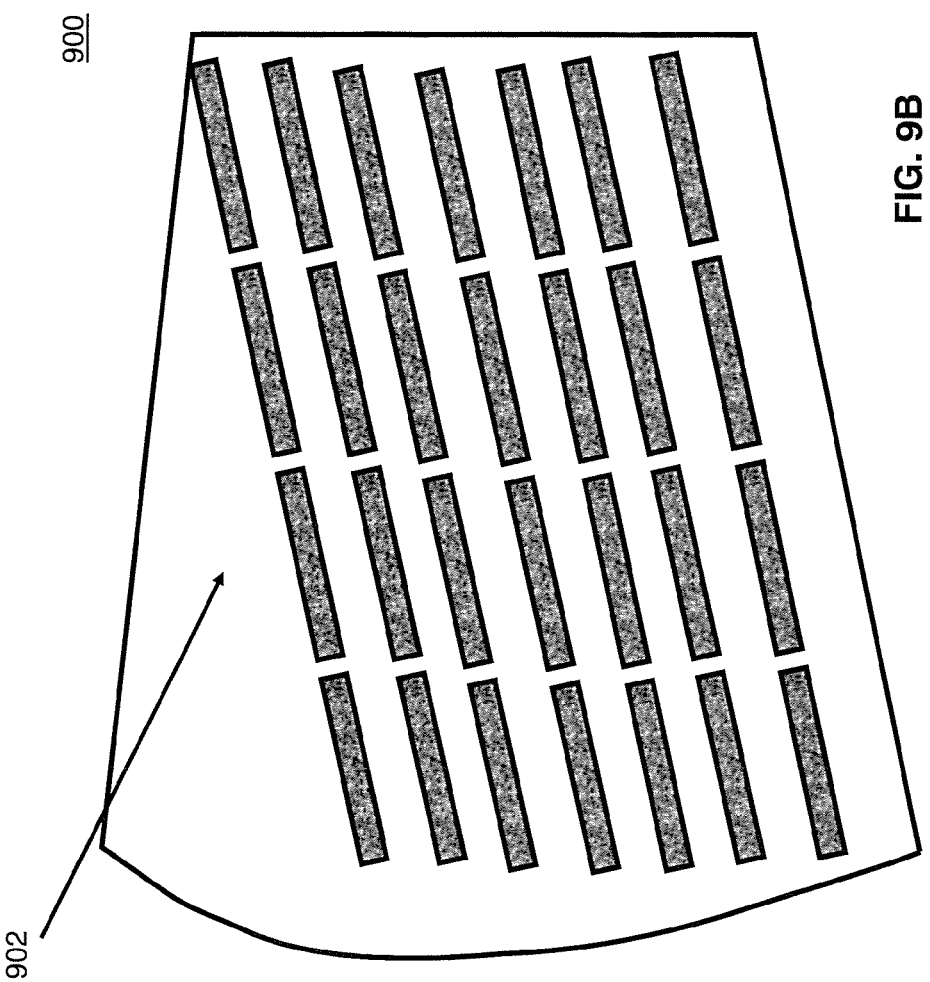
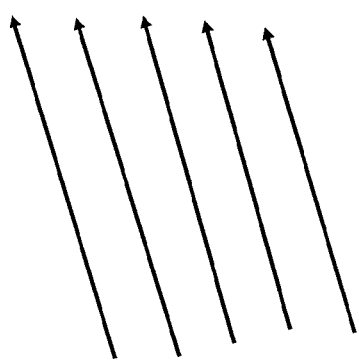
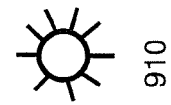
FIG. 9B

SYSTEMS AND METHODS FOR GROWING VEGETATION

CROSS REFERENCE TO RELATED APPLICATION(S)

This application is a 35 U.S.C. § 371 National Phase Entry Application from PCT/IB2017/050854, filed Feb. 16, 2017, designating the United States and claiming priority to U.S. Provisional Application No. 62/295,893, filed on Feb. 16, 2016, the full disclosures of which are incorporated herein by reference in their entirety.

TECHNICAL FIELD

Aspects of this disclosure relate generally to green energy production and storage techniques, and more particularly, to systems and methods for the efficient growth of vegetation.

BACKGROUND

Anaerobic digestion (AD) is a technique for converting organic matter into biogas, and ultimately, methane gas. Methane is the primary component of natural gas, which provides an increasing percentage of centralized power generation. Certain products utilizing anaerobic digestion have been deployed in attempts to reduce greenhouse gas emissions. These products have been mainly directed towards treating unwanted by-products, such as animal excrement or slurry as well as industrial and domestic food waste. However, the present disclosure recognizes that vegetation, including for instance, grass, green garden waste and weeds, also represents a valuable source of high energy content organic matter.

In particular, vegetation can be a high energy feedstock for anaerobic digestion. However, the land available for its growth and harvesting is limited as it is used primarily for animal grazing for meat and dairy products.

SUMMARY

Accordingly, there is a need for systems and methods to increase the growing area for vegetation. The vegetation can be used, for examples, as a feedstock in an anaerobic digestion process.

According to some embodiments, a system for growing vegetation is provided. The system includes a rotating growth mat and a cutting device. In certain aspects, the system includes a plurality of rollers, where the rotating growth mat is suspended vertically from at least one of the plurality of rollers. The system may be configured such that the mass of the mat on a growth side is greater than the mass on an inhibited side, and thus, as a result, the growth side naturally falls downward while the inhibited side moves upward. Mechanical energy from this movement may be captured and used to facilitate additional operations related to the operation of the system.

According to some embodiments, a method is provided for operating a vertical growth system for vegetation. The method includes the steps of obtaining electricity from an external source; operating an artificial light source using the electricity, where the light source is configured to deliver light energy to a growth surface of a vertical growth mat; and operating a cutting device, where the cutting device is configured to cut vegetation grown on the growth surface of the vertical growth mat. In some aspects, the electricity is obtained at a below-average cost due to one or more of time of day and season, and the external source is one or more of a wind, solar, tidal, and hydro-electric source. The growth system may be operated to provide both natural and artificial light in order to accommodate continuous growth of the vegetation. Additionally, the position of one or more of the vertical growth mats may be varied based on the position of the sun to improve growth efficiency.

According to some embodiments, a method is provided for operating a growth system for vegetation. The method includes the steps of delivering nutrients to one or more vertical growth mats of a vertical growth system. The nutrients may include, for example one or more of fertilizer and/or water. The method may also include delivering light energy to the one or more growth mats. In certain aspects, the light energy may be from an artificial and/or natural light source. Additionally, the method may include operating a cutting device to cut vegetation grown on the growth mats. According to some embodiments, at least one of the vertical growth mats of the system is suspended vertically on a roller. In certain aspects, the delivering nutrients and/or delivering of light energy is performed such that a first mass of vegetation grown on a first side of the growth mat is greater than a second mass of vegetation grown on a second side of the growth mat. As a result, the first side falls downward and the second side moves upward.

In some embodiments, vertical growth mats may be arranged in a stacked configuration to further increase the effective growing area. For example, a growth system may include a plurality of rollers, one or more artificial light sources, and a plurality of growth mats. The growth mats can be arranged such that a first set of mats is located above a second set of mats. The system may further include one or more cutting devices and an anaerobic digestion system, where the anaerobic digestion system is configured to operate using vegetation grown on the vertical growth mats and processed by the cutting device.

In some embodiments, a system for growing vegetation offshore is provided. The system may include, for example, one or more rotating growth mats, a cutting device configured to cut vegetation grown on one or more surfaces of the rotating growth mats, and an anaerobic digestion system configured to operate using the vegetation grown on the rotating growth mats and processed by said cutting device. The mats, cutting device, and anaerobic digestion system are located on an offshore platform. In some embodiments, one or more artificial light sources a further provided, where at least one of the artificial light sources is powered by a renewable source located at the offshore platform, such as a wind, solar, tidal, and/or hydro-electric electricity source.

In some embodiments, a method for the processing of biogas is provided. The method may include generating liquid air, for instance, using one or more of wind, hydro, solar, tidal, and/or wave power sources. These sources can directly power the process, or alternatively, generate electricity to power the process. The method also includes obtaining biogas, for instance, from an anaerobic digestion process. In some examples, the biogas cab be obtained by performing anaerobic digestion on vegetation obtained from a vertical growth mat. The method also includes creating carbon dioxide and methane from the biogas using the liquid. In some embodiments, this includes passing the liquid air and biogas through a heat exchanger to form liquid methane and liquid carbon dioxide. Additionally, the method can include operating a cryogenic milling device to disintegrate vegetation, where the milling device uses liquid air or a derivative of liquid air, such as liquid nitrogen.

The above and other aspects and embodiments are described below with reference to the accompanying drawings.

BRIEF DESCRIPTION OF THE DRAWINGS

The accompanying drawings, which are incorporated herein and form part of the specification, illustrate various embodiments of the present disclosure and, together with the description, further serve to explain the principles of the disclosure and to enable a person skilled in the pertinent art to make and use the embodiments disclosed herein. In the drawings, like reference numbers indicate identical or functionally similar elements.

FIGS. 9A-9D illustrate layouts in accordance with exemplary embodiments.

DETAILED DESCRIPTION

Figure 1:
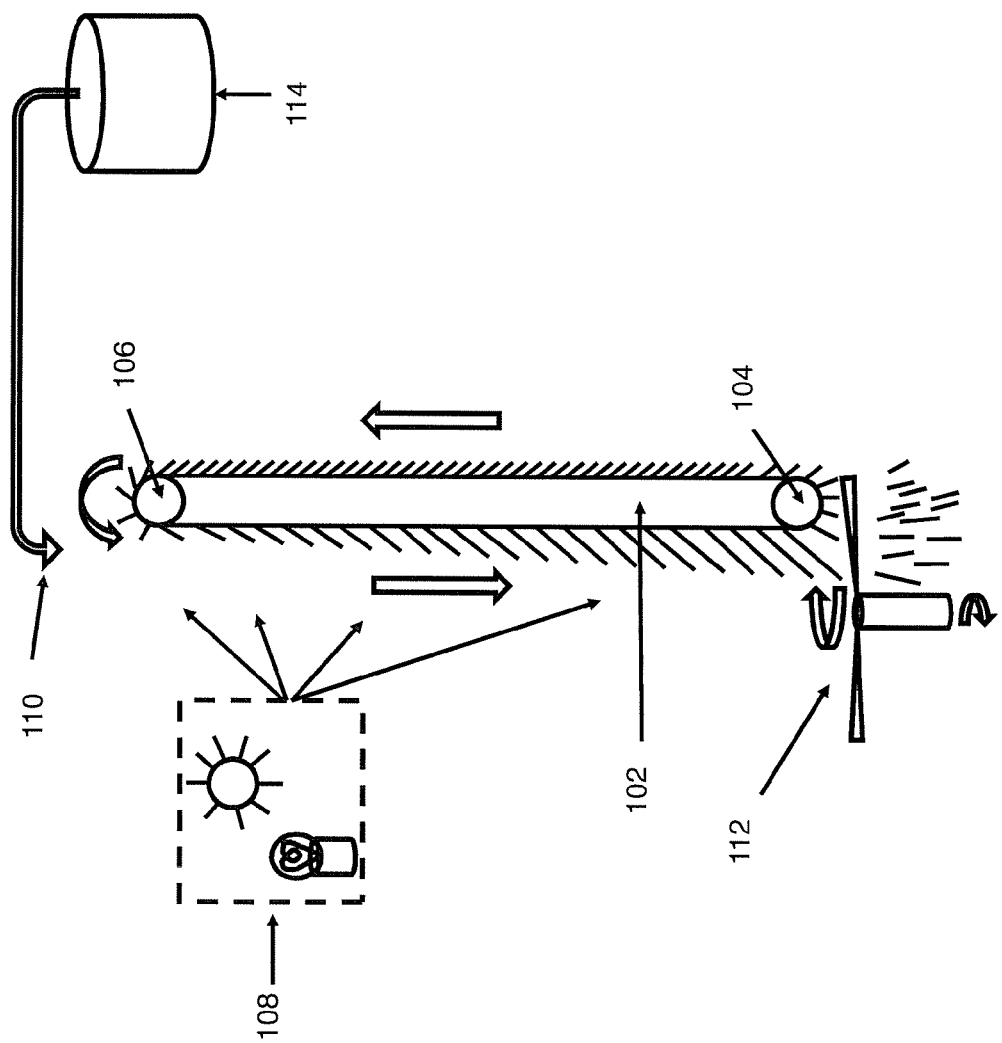
FIG. 1 is a schematic of a vegetation growth system in accordance with some embodiments.

Referring now to FIG. 1, a system 100 for the growth of vegetation is shown in accordance with some embodiments. The system 100 includes one or more rotating growing mats 102. In certain aspects, the mats may be suspended vertically. In some embodiments, the mats are arranged between rollers 104 and 106. The growth of vegetation on a particular side of the mat may be encouraged by the appropriate application of light and nutrients, for example, water. The light may be provided by one or more natural and/or artificial light sources 108. For example, the light may be provided by the sun and/or one or more light emitting diodes (LEDs). According to some embodiments, the LEDs are red and/or blue and may be high efficiency.

In the system 100, water and other nutrients may be provided, for example, by a nozzle 110. According to some embodiments, the nozzle 110 is positioned on an optimized growth side. In this example, as the vegetation moves into the region of increased light levels, ideal conditions for the rapid vegetation growth are provided and the growth process is maintained. In certain aspects, on the other side of the mat 102, growth continues but at a lower rate due to the lower availability of water, nutrients, and/or light. The nutrients and/or water may be obtained, for instance, from storage 114.

In certain aspects, the mat comprises a growth side and an inhibited side. For instance, the side exposed to light, water, and/or nutrients may be a growth side, while the other side is an inhibited side. In some embodiments, the inhibited side may be shielded from one or more of nutrients, light, and/or water. The rollers 104, 106 can be configured such that a mass of the mat's growth side is greater than a mass on the inhibited side, and as a result, the growth side falls downward and the inhibited side moves upward. For instance, the mass of vegetation grown on a first side may be greater than the mass of vegetation grown on the inhibited side. In this way, the mat rotates according to the growth of the vegetation.

Some embodiments may require mat 102 to be made of a very strong and rot free material, as it may need to support the weight of the growing medium as well as the vegetation leaf. In certain aspects, it should not be susceptible to excessive stretching or degradation. According to some embodiments, growing mat 102 has a first side and a second side. The first side may include, for instance, a backing layer and the second side may include, for instance, a plurality of growing pockets. In certain aspects, these may be comprised of porous Kevlar and cotton wool and containing a seeded growing compost. Specifically, in some embodiments, a strong backing layer is provided with a series of growing pockets made from porous Kevlar netting stitched onto the outermost side. A low density material such as cotton wool mixed with a seeded growing compost fills the pockets and is used initiate the growing process. Once the root system is fully established through the Kevlar netting, the pockets effectively become a single growing layer.

System 100 may further include a cutting device 112, such as, for example, a rotating blade or strimming implement. The cutting device 112 may be located, for instance, below mat 102, and in some instances, below roller 104. The cutting device may be integral to the other components of system 100, or moveable. For instance, the cutting device may be moveable such that it may be used on multiple growth mats. The cutting device 112 can be used to release the excess vegetation from the mat 102, for instance, at the bottom of the optimized growth side. However, the cutting device 112 can also be located on a side of the growth mat 102. According to certain aspects, the mass of the mat on the optimized growth side is greater than the inhibited side such that the mat falls downwards on the optimized side and upwards on the inhibited side.

Figure 2:
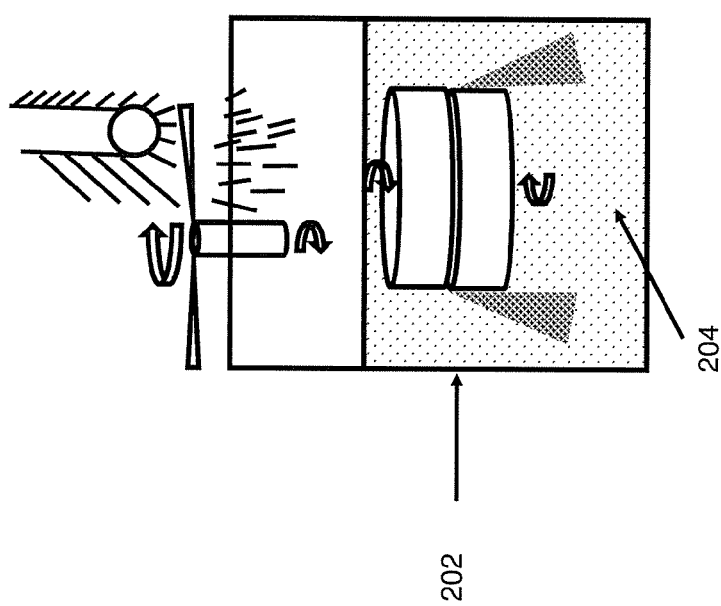
FIG. 2 is a diagram of a cutting device in accordance with some embodiments.

According to some embodiments, the cutting device 112 is optimized to provide partial processing of the vegetation for use as feedstock. In some applications, it may be important for maximum conversion of plant matter to methane and carbon dioxide that the vegetation is cut into the smallest pieces possible to allow anaerobe microscopic organisms access to the inside of the cellular structure such as cellulose, etc. For example, and as illustrated in FIG. 2, the processing of the vegetation may be optimized through the use of a cryogenic milling mechanism 202. The mechanism 202 may be part of cutting device 112, in some embodiments. In this example, the cut vegetation is frozen to cryogenic temperatures, where the cell structure can be further disintegrated through crushing action on the now brittle plant material. The freezing may be accomplished, for instance, using liquid nitrogen or liquid air 204. After freezing, and in certain aspects, the thawing process of the vegetation may rupture the cell walls of the vegetation.

In certain aspects, the rotating growth mat 102 is arranged such that mechanical energy is released as the mat rotates, for instance, as the heavier side of the mat lowers itself. This energy can be captured and used for at least one of powering the cutting device, moving at least one of said plurality of rollers, powering a conveyor belt, and powering a compressor. In some embodiments, the mechanical energy can be captured through a suitably geared mechanism that uses the mats unbalanced weight as a potential energy reservoir. The stored potential energy in the growing mat could be used to increase the overall efficiency of the system by being used, for example, to power the cutting device 112 to remove another strip of vegetation from the bottom of the mat, move the position of the rollers, power a conveyor belt collecting the released foliage, pump nutrients back up to the top roller position, and/or power a compressor used in the preprocessing of the vegetation feedstock of the cleaning and liquefaction of the resulting biogas from a following anaerobic digestion process. This energy could also be stored in a large spring similar to that of a clock so that when built up over time it can be released through a suitable control circuit or other mechanism. The stored energy could be used, for example, at night time to power a generator, for instance, to provide the light that can be used to maintain the photosynthesis of the grass during night time hours or when it is cloudy.

According to some embodiments, a growing, falling/rotating, and cutting process is repeated continuously. For instance, as long as the mat on the optimized growth side is heavier than the inhibited growth side, it will cause indefinite rotation of the mat provided that there are nutrients, water, and/or light available to the optimized growth side.

Intermittent renewable energy sources such as wind, solar, tidal, hydro-electric and wave power may be used in the systems of certain embodiments. However, such sources may have the limitation that they will often produce electricity when there is not a requirement for it, such as at night or during more favorable seasonal months when demand is lower. According to some embodiments, there are periods when this electricity could be purchased at low cost and converted into light that can be used to store energy during these hours through photosynthesis. For instance, using the system of one or more of FIGS. 1, 3, 4, and 10. In particular, some embodiments can make use of both natural light and artificial light.

Figure 3:
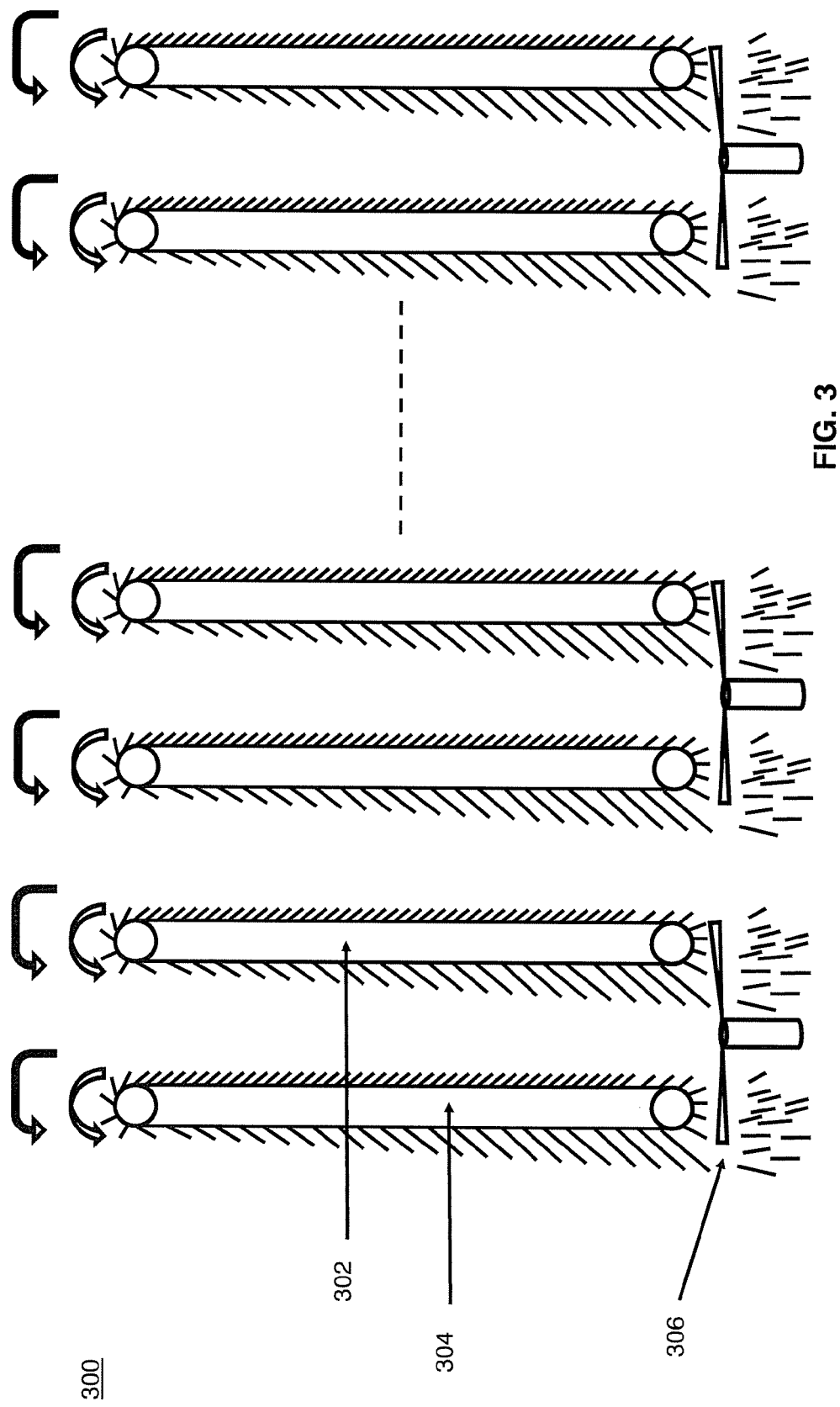
FIG. 3 is a schematic of a vegetation growth system in accordance with some embodiments.

Referring now to FIG. 3, a growing arrangement 300 is provided which uses a plurality of growing mats 302, 304. For instance, a plurality of systems 100 may be arranged together in series. As illustrated in FIG. 3, the growing mats 302, 304 may be arranged in a row (1, 2 . . . n mats) to increase the growing area available for a given land area dramatically. This results in a corresponding increase in the yield of vegetation and the resulting anaerobic digester products per unit area. According to some embodiments, a cutting device 306 may be used to extract vegetation from more than one mat at the same time.

Figure 4:
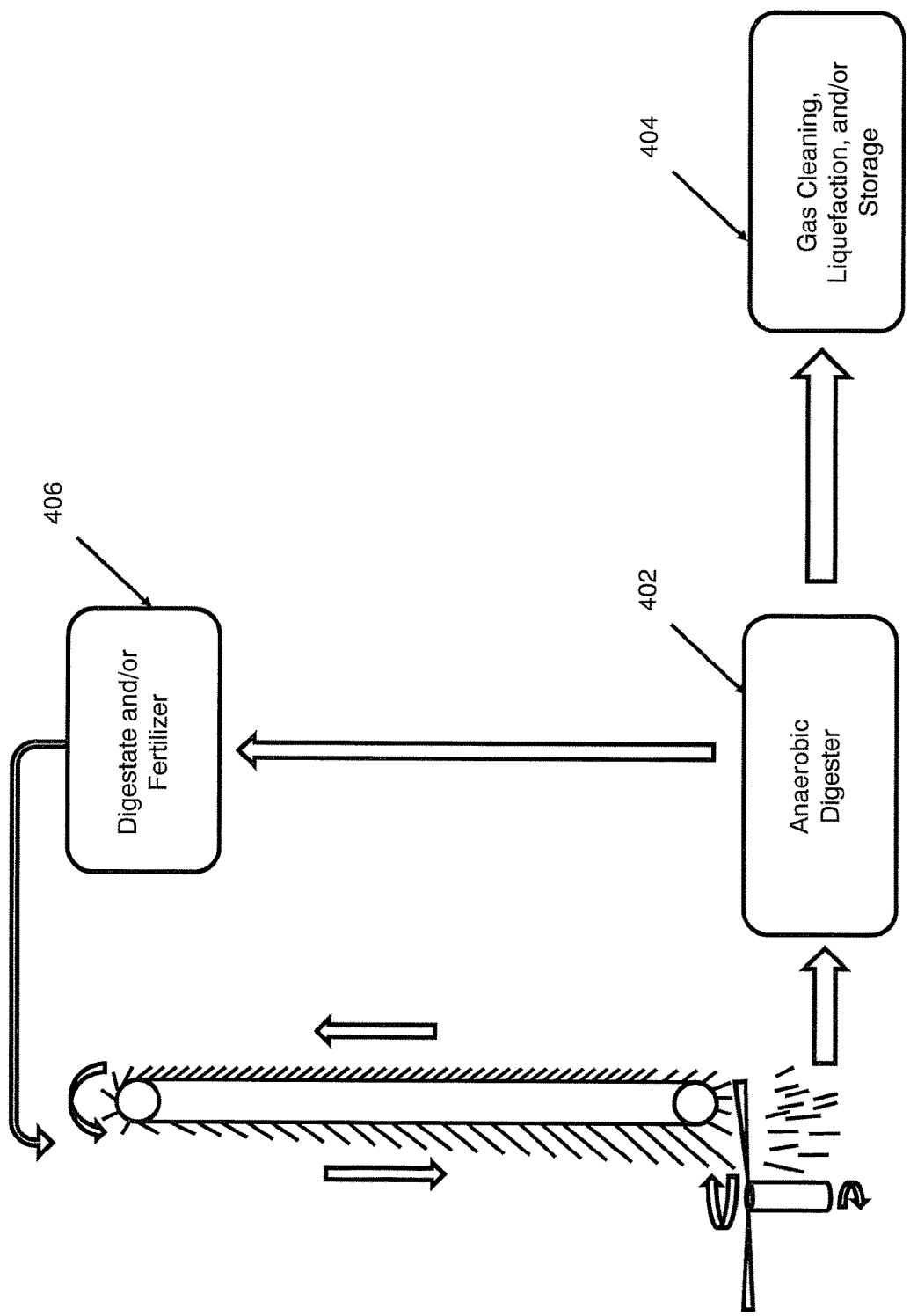
FIG. 4 is a schematic of a vegetation growth and methane generation system in accordance with some embodiments.

Referring now to FIG. 4, a system 400 for generating a gas or liquid, such as methane, is provided in accordance with some embodiments. In this example, one or more growing mats may be used in connection with an anaerobic digestion process. For instance, a system 100 as described with respect to FIG. 1 can be coupled to an anaerobic digester 402. According to some embodiments, the released vegetation can be used as the substrate fed to an anaerobic digester, which can be further processed. For instance, anaerobic digester 402 can be coupled to a gas cleaning, liquefaction, and/or storage stage 404. Additionally, the vegetation may be processed to make digestate and/or fertilizer, which can be stored 406. The storage of digestate and/or fertilizer made from the vegetation of system 100 may be, for instance, storage 114 of FIG. 1. In certain aspects, the methane and carbon dioxide generated through the anaerobic digestion, cleaning, and/or liquefaction processes are valuable products, and the digestate and/or fertilizer can be used to complete the growing cycle.

Figure 5:
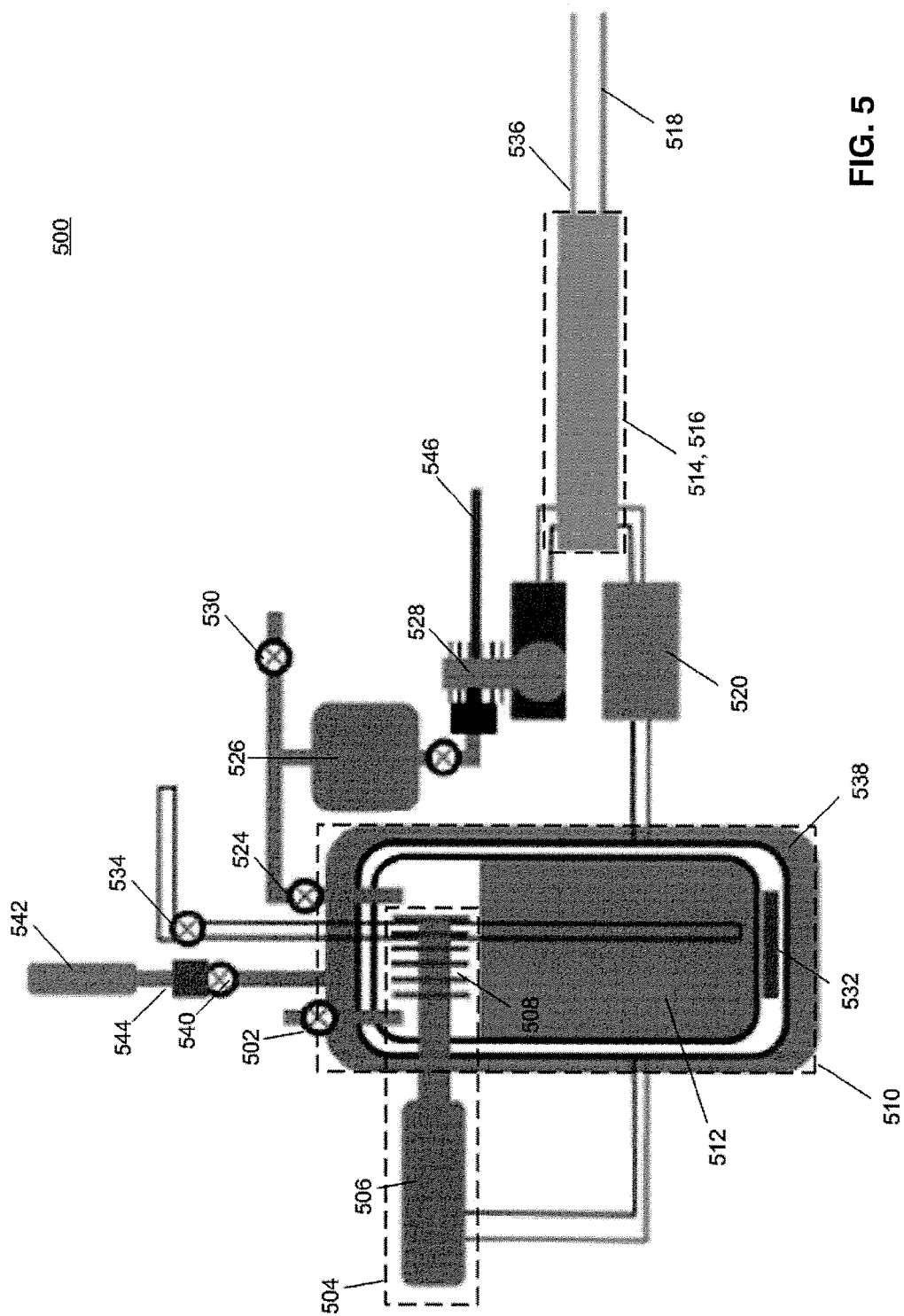
FIG. 5 is an illustration of a methane processing and storage unit in accordance with exemplary embodiments.

According to some embodiments, one or more of anaerobic digestion 402, and gas cleaning, liquefaction, and/or storage 404 can be performed, for example, using system 500, which is illustrated in FIG. 5. System 500 may be, for instance, a part of a micro-anaerobic digestion (micro-AD) unit.

According to some embodiments, system 500 includes at least one inlet valve 502. Methane gas or liquid methane gas may be introduced into storage vessel 510 via the inlet valve 502. The storage vessel 510 may be, for instance, a Dewar. A cooling unit 504 is configured to cool the methane gas or liquid methane gas within the storage vessel 510. The cooling unit may include, for instance, a closed cycle refrigerator 506 and closed cycle refrigeration head 508. In certain aspects, when the head 508 is cooled to a temperature below the condensing temperature of methane gas, liquid methane condenses on the head 508. The condensed liquid methane will run off head 508 into the main liquid methane reservoir 512.

In some embodiments, mains electricity is available to the system 500. For instance, a mains power line 518 may be attached to a power supply/inverter 514, which is used to maintain a power storage device, such as battery 520, at a maximum charge level. In certain aspects, a microcontroller 516, which may include one or more processors, is also provided and attached to power line 518. One of skill in the art will recognize that the power supply/inverter 514 and microcontroller 516 may be provided as a single unit, or alternatively, as independent devices. The unit may also include one or more transceivers and antennas connected to microcontroller 516, for instance, to enable communication with external devices, such as a central controller, other micro-AD units, or user electronics. One or more of the battery 520 and power supply/inverter 514 can be used to power cooling unit 504, for instance, providing power to closed cycle refrigerator 506 to manage boil-off of the liquid methane of reservoir 512. For example, the refrigerator 506 can be controlled to prevent any boil-off of the liquid methane of reservoir 512. According to this embodiment, the storage period of the liquid methane may be indefinite, as the unit can be configured such that there is no pressurization occurring within reservoir 512.

The system 500 may include a pressure valve 524 to release boil-off methane. For instance, the valve 524 may be configured to release boil-off at a preset level into a buffer reservoir 526. The gaseous methane of the buffer reservoir may be used as fuel for one or more power generators of the system 500. For example, when the buffer reservoir reaches maximum capacity, or any pre-determined level, a power generator 528 may be started and powered by the gaseous methane of buffer reservoir 526. The power generator may be any source capable of providing sufficient electrical power to cooling unit 504, such as an internal combustion (IC) generator or fuel cell. Additionally, the power generator may provide power to cutting device 112 or a light source 108. In certain aspects, the IC engine output power may be sized such that sufficient electrical power is generated to allow full charging of battery 520 while simultaneously providing sufficient power to the closed cycle refrigerator 506. The generator 528 may include a $CO_2$ and/or $H_2O$ exhaust 546.

In some embodiments, it may be necessary that the system 500 is configured for the extraction of methane gas "on-demand." The on demand extraction of energy may be, for example, to power one or more components of system 100, 300, 400, and/or 1000. For instance, to power a cutting device and/or artificial light source. This extraction may be through a main output valve 530. Further, an internal heater 532, such as a resistive heater, of the main reservoir 512 can be used to intentionally increase boil-off and increase Dewar pressure for release of either methane gas or liquid methane. Liquid methane can be released through a liquid methane take-off port 534. Alternatively, this heat could be supplied by reversing the closed cycle refrigerator 506 polarity such that it draws heat from the outside of the Dewar and transfers it to the main reservoir.

In some embodiments, internet connectivity 536 can be incorporated to allow the microcontroller 516 to send a status update or alarm to the unit owner or supplier. This also allows for remote control or inspection of the system to be carried out by the owner or supplier. Additionally, while the main Dewar can utilize a vacuum for maximum insulating properties and minimal boil-off, an outer layer of solid insulation 538, such as low density polystyrene or other insulating material, can be incorporated to limit the excess boil-off resulting from a sudden loss of vacuum. The generator 528 can be rated to readily accept all boil-off resulting from such a scenario with all energy diverted to the coldhead 508 or resistive ballast in the microcontroller 516 as appropriate. In some embodiments, the system 500 may be provided with additional safeguards such as a high pressure release valve 540. Such a safeguard may be used, for instance, following a failure of the closed cycle refrigerator 506 and simultaneous failure of the generator 528. The boil-off may flow to a flame containment vessel 542, such as a metal gauze cavity. The pressure release valve 540 can be configured to trigger a mechanical igniter 544 to ignite the resulting boil-off converting the methane to $CO_2$ and $H_2O$ in a controlled flare.

Figure 6:
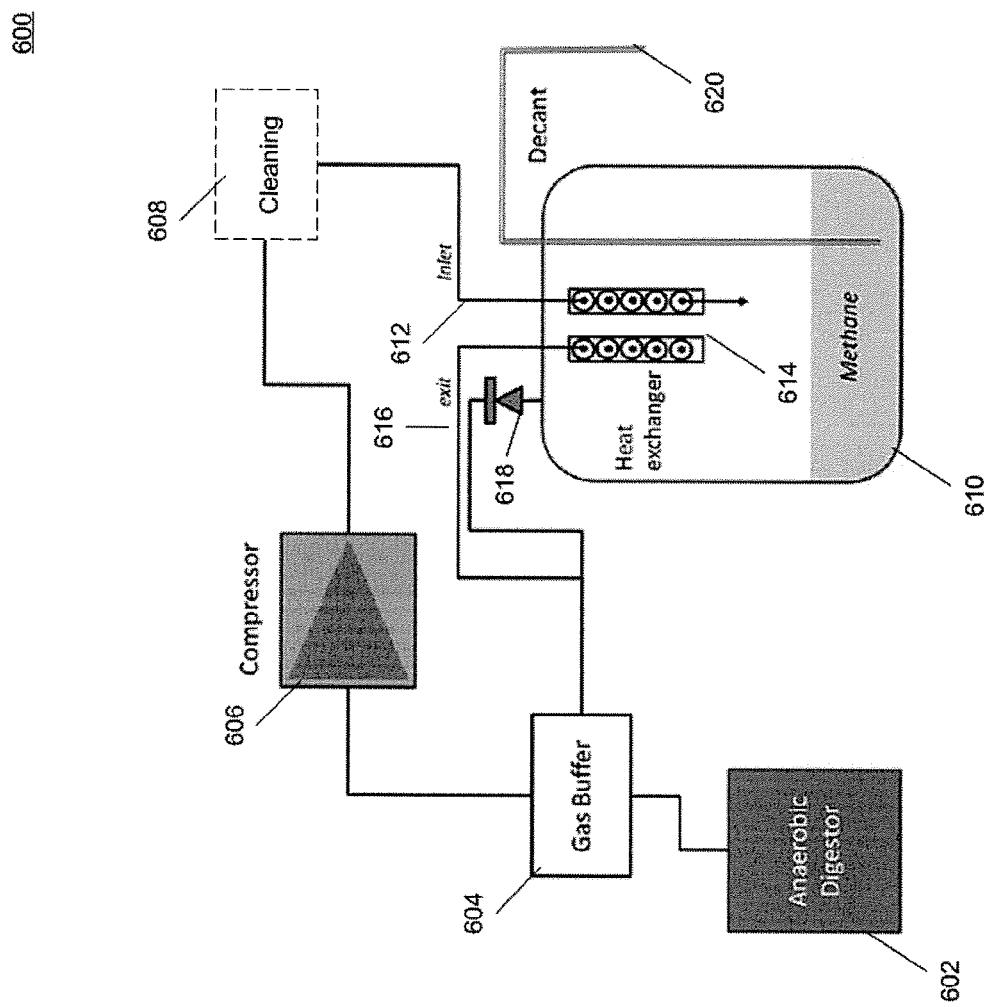
FIG. 6 is an illustration of a methane processing and storage unit in accordance with exemplary embodiments.

Referring now to system 600 of FIG. 6, in some embodiments, gas generated in an anaerobic digester 602 can be stored in a gas buffer 604 and tank 610. This may correspond, for instance, to anaerobic digestion 402, and gas cleaning, liquefaction, and/or storage 404 in FIG. 4.

The gas may be stored in the buffer 604, for example, until a predetermined pressure is reached. In some embodiments, a compressor 606 is started and the gas is circulated from the buffer through the compressor 606. The compressor 606 may be started, for example, once the predetermined pressure in buffer 604 is reached. The compressed gas may then be passed to an optional cleaning stage 608. The compressed gas is circulated to a storage tank 610 via inlet 612 that includes a heat exchanger 614. In some embodiments, heat exchanger 614 may include finned heat exchanger tubing. According to certain aspects, the gas may be expanded through an orifice of heat exchanger 614 for cooling, or alternatively, a variable needle valve. After expansion, liquefied methane collects in the storage tank 610, which may be, for example, a Dewar. The remaining gaseous methane, i.e., the non-liquefied methane, returns to gas buffer 604 via exit 616. The system 600 may also include one or more control valves 618 to regulate pressure and control gas flow. The liquid methane may be removed from storage tank 610 as needed, for instance, via a decanter 620.

Figure 7:
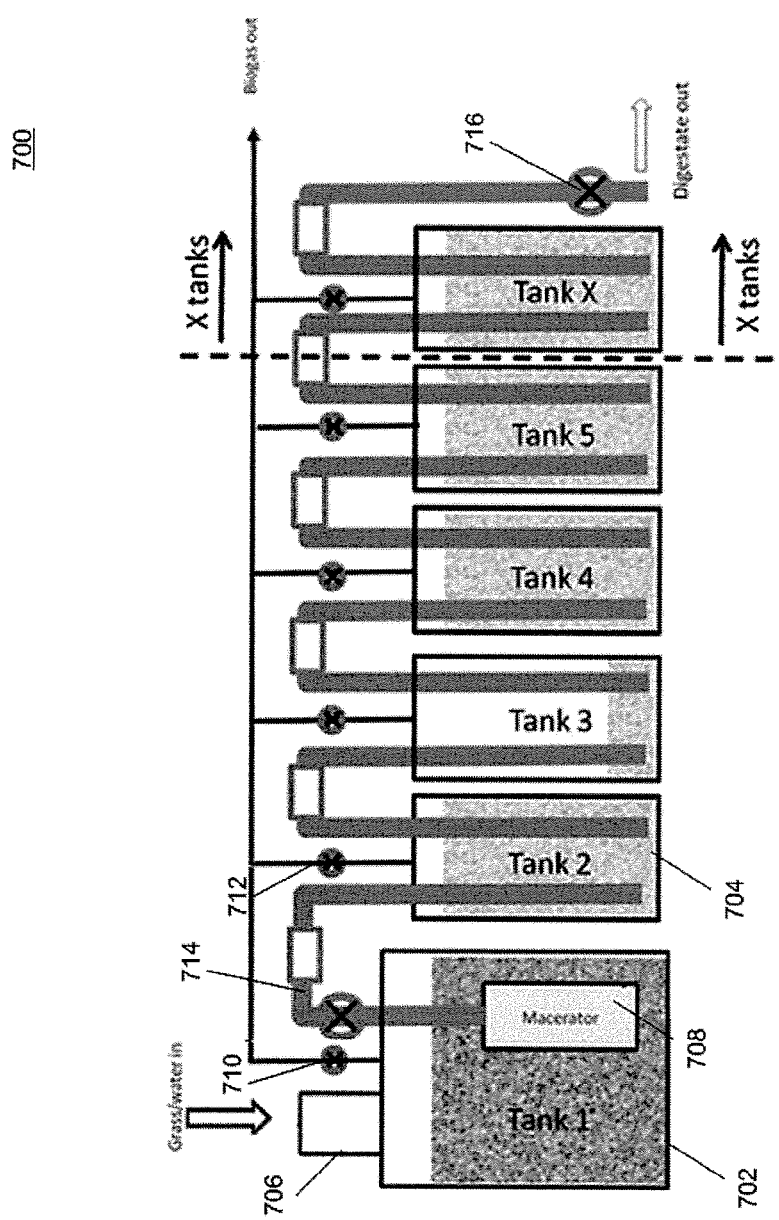
FIG. 7 is an illustration of an anaerobic digester in accordance with exemplary embodiments.

Referring now to FIG. 7, an anaerobic digester 700 according to certain embodiments is illustrated. In some embodiments, the anaerobic digester of FIG. 7 may be a part of system 400, and coupled to storage system 500. For instance, digester 700 can provide the input to system 500 at inlet 502. In this example, the anaerobic digester 700 comprises multiple tanks (702,704); however, digester 700 could include of a single tank 702. In certain aspects, the tanks may be relatively small, and the total number of tanks may be set according to a customer's intended use and/or the amount of land that will be used to supply feedstock. In certain aspects, a PH gradient and temperature gradient can be maintained across the tanks. The digester 700 may further include an inlet 706 for receiving feedstock and, optionally, a macerator 708 to mulch, agitate and/or separate components of the feedstock during anaerobic digestion. The inlet 706 may receive vegetation as a feedstock, for instance, from growth mat 102. In some embodiments, the vegetation from growth mat 102 may be cut by cutting device 112 prior to input to digester 700. In some embodiments, the feedstock input to digester 700 may be a combination of grass and/or water; however, digester 700 is not necessarily limited to such an input. Additionally, in some embodiments, the processing of the vegetation used in digester 700 may be optimized through the use of cryogenic milling mechanism 202, as illustrated in FIG. 2.

In some embodiments, the gas output from each tank is controlled via a latching gas valve 710,712. In certain aspects, the valve may be remotely controllable, for instance, via local or remote computer. If a quantity of substrate (e.g., partially digested feedstock) is required to be moved from one tank to the next, for instance, from tank 702 to tank 704, the gas output of the sending tank 702 can be turned off using gas valve 710. However, the gas output valve 712 of the receiving tank 704 is left open. The gas pressure in the sending tank 702 is then allowed to build up and as a result the substrate is forced though the outlet pipe 714 and into the receiving tank 704. Once the substrate move has taken place, the gas pressure from the sending tank 702 is relieved to a point at which transfer stops. The gas pressure may then be maintained at this level to prevent re-syphoning of the substrate. In some embodiments, the pressure can be completely released to allow the levels of the tanks 702,704 to re-equalize. In some embodiments, one tank of digester 700 is left intentionally empty. In certain embodiments, at least one tank is always left empty.

According to certain aspects, the process is returned to an aerobic digestion state to compost any residual organic matter and/or remove any unpleasant odors before expelling the digestate, for instance, via an outlet valve 716. In some embodiments, digestate and/or fertilizer generated in an anaerobic digestion process, for instance in digester 700, can be used in connection with vegetation growth as illustrated in FIG. 4. For example, digestate and/or fertilizer 406 may be obtained from digester 700.

According to some embodiments, pressure in the final tank or "stage" of a multi-tank/stage anaerobic digester, such as digester 700 of FIG. 7, can be allowed to build up to a desired pressure. Pressure build-up can be controlled, for example, by adjusting one or more valves of the digester and/or increasing temperature. In certain aspects, the desired pressure is high enough that a compressor in subsequent processing stages is not required. For instance, if the pressure is allowed to build to a high enough level, for example between 2 and 30 bar, it may be possible to eliminate compressors that would otherwise be needed during cleaning or liquification, such as compressor 808 of FIG. 8 or compressor 606 of FIG. 6. The specific pressure required, however, will depend on the configuration of one or more of the digester and subsequent stages. Referring to FIG. 6, in some embodiments, the pressure in a final stage of anaerobic digester 602 can be allowed to increase such that naturally pressurized biogas is fed to heat exchanger 614, which may include finned heat exchanger tubing. Similarly, with respect to the example of FIG. 8, naturally pressurized biogas may by passed through filter 816 onto heat exchanger 812, which may also include finned heat exchanger tubing. Accordingly, the cleaning and/or liquification process can be effectively powered by the anaerobic digestion process itself and the associated microbes. This may include, for example, gas cleaning, liquefaction, and/or storage 404 of system 400, as illustrated in FIG. 4.

Figure 8:
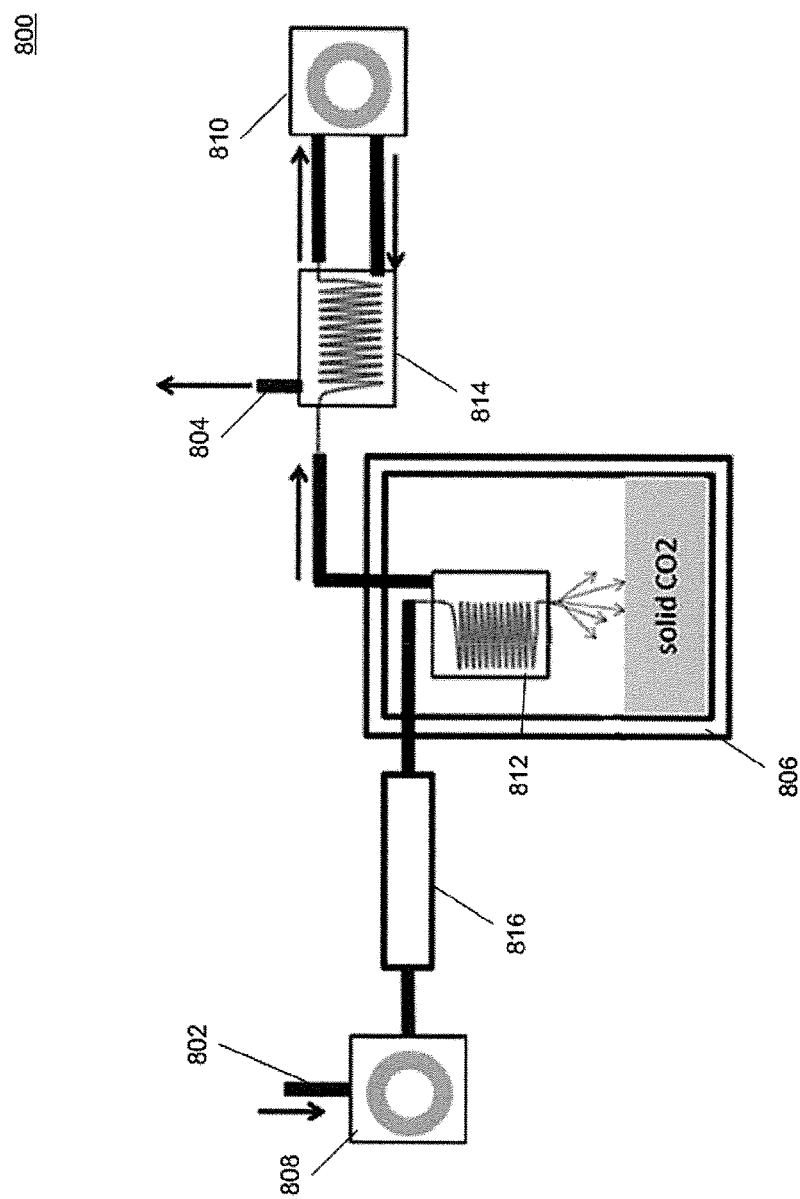
FIG. 8 is an illustration of a methane cleansing system in accordance with exemplary embodiments.

Referring now to FIG. 8, an exemplary $CO_2$ removal stage 800 is provided. The removal stage 800 includes an inlet 802, and outlet 804, and a $CO_2$ storage unit 806. The stage 800 further includes a number of compressors (808,810) and heat exchangers (812,814), as well as an optional hydrogen sulphide filter 816. The inlet 802 is connected to a biogas source. For instance, inlet 802 may be connected to anaerobic digester 700 illustrated in FIG. 7. Outlet 804 may be coupled to a methane storage unit, such as system 500. For instance, outlet 804 may be connected directly to input valve 502.

According to some embodiments, cryogenic cooling grinding and/or milling of the vegetation material, for instance as illustrated in FIG. 2, can provide a pre-treatment of feedstock. Cryogenic pre-processing of vegetation can improve methane yield in subsequent processing. In certain aspects, the cryogenic processing explodes the individual plant cells through the expansion of the water within the cytoplasm releasing the inner readily anaerobically digestible organic contents from the lignin rich outer cell wall, which can be difficult for the anaerobes to digest. The expansion may occur, for instance, as part of a thawing process. This can greatly increase the biogas, and therefore methane yield, and also reduce the retention time, thereby increasing throughput. Such a process could, for example, improve the performance of system 400.

Figure 9A:
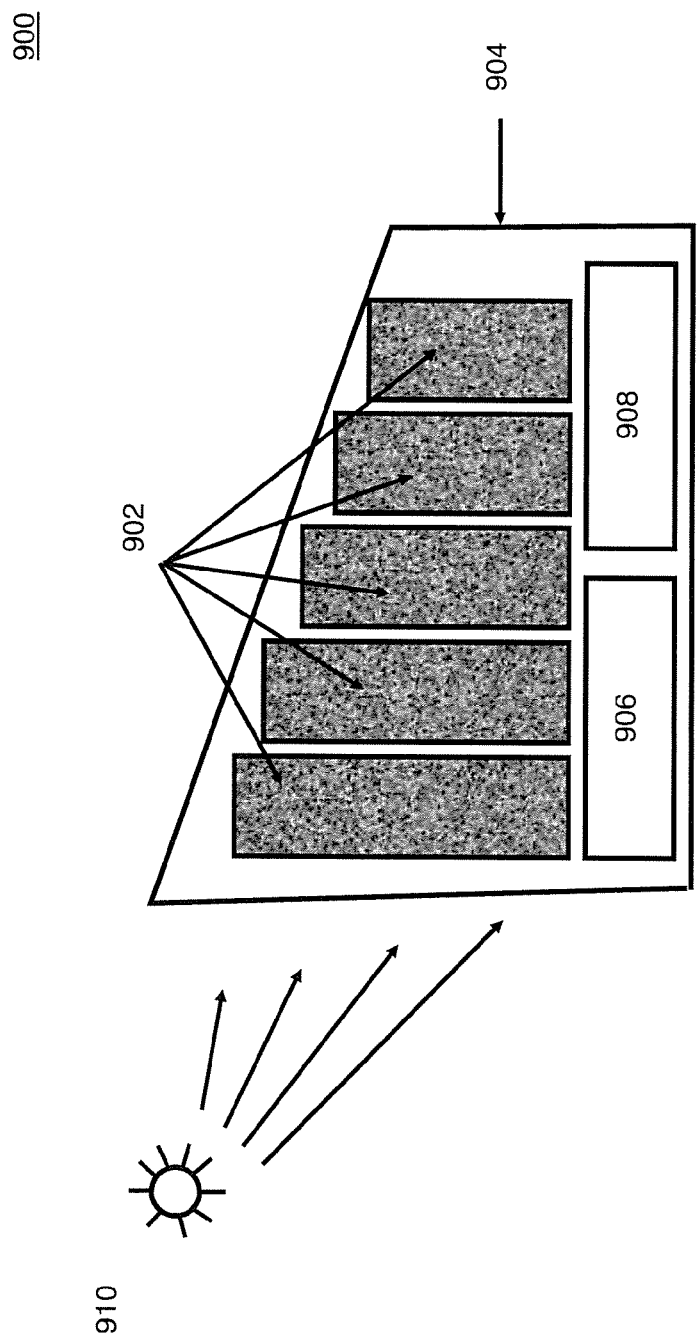
Figure 9C:
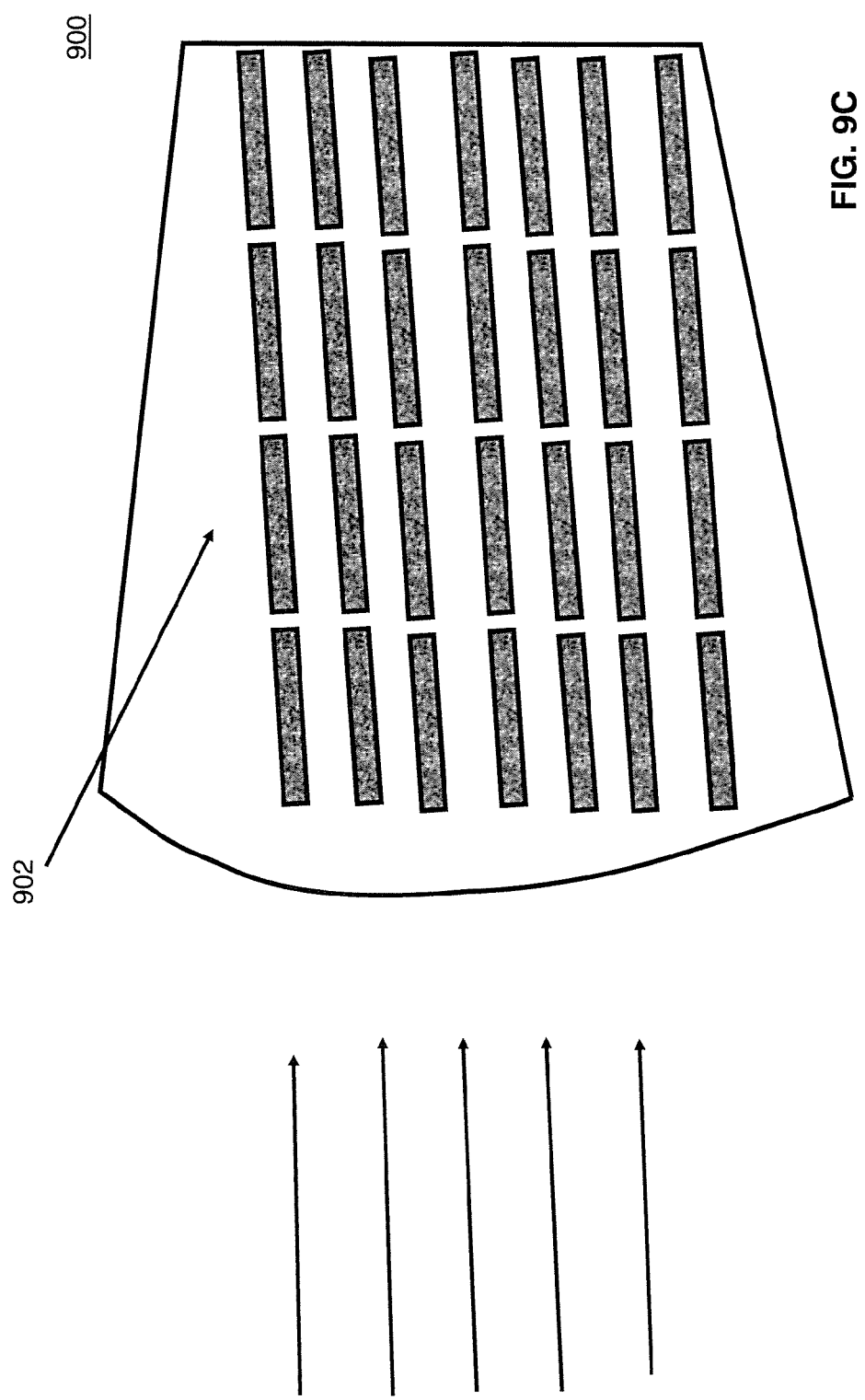
Figure 9D:
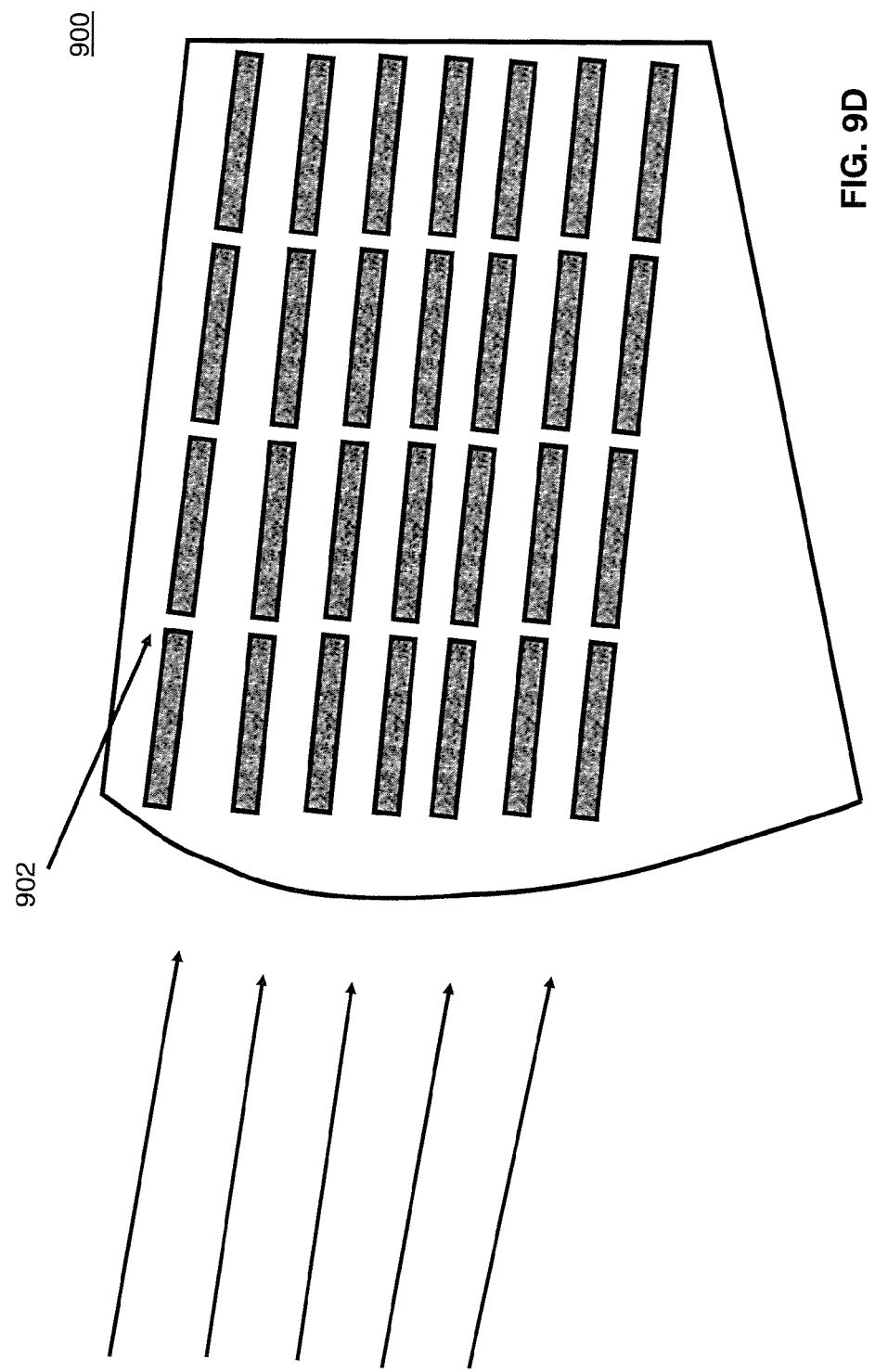

Referring now to FIGS. 9A-9D, growing layouts according to some embodiments are provided. With respect to FIG. 9A, a layout 900, for instance in greenhouse 904, is illustrated in a side view. In this example, mats 902 are arranged in greenhouse 904 with light source, e.g., the sun, 910. In some embodiments, an anaerobic digester 906 and gas cleaning, liquefaction, and/or storage stage 908 are co-located with the mats 902. In certain aspects, the position of one or more of mats 902 can be varied. The varying is performed, for instance, based on the position of the sun 910 to improve growth efficiency. For instance, as illustrated with respect to FIG. 9B, a top view of layout 900 is shown with mats 902 positioned based on the location of the sun 910. This layout may correspond, for instance, to a morning time. Referring now to FIG. 9C, the position of mats 902 may be varied as the location of the sun 910 changes. This layout may correspond, for instance, to midday. Referring now to FIG. 9D, the position of mats 902 may be varied again as the position of location of the sun 910 as it changes. This layout may correspond, for instance, to evening.

Figure 10:
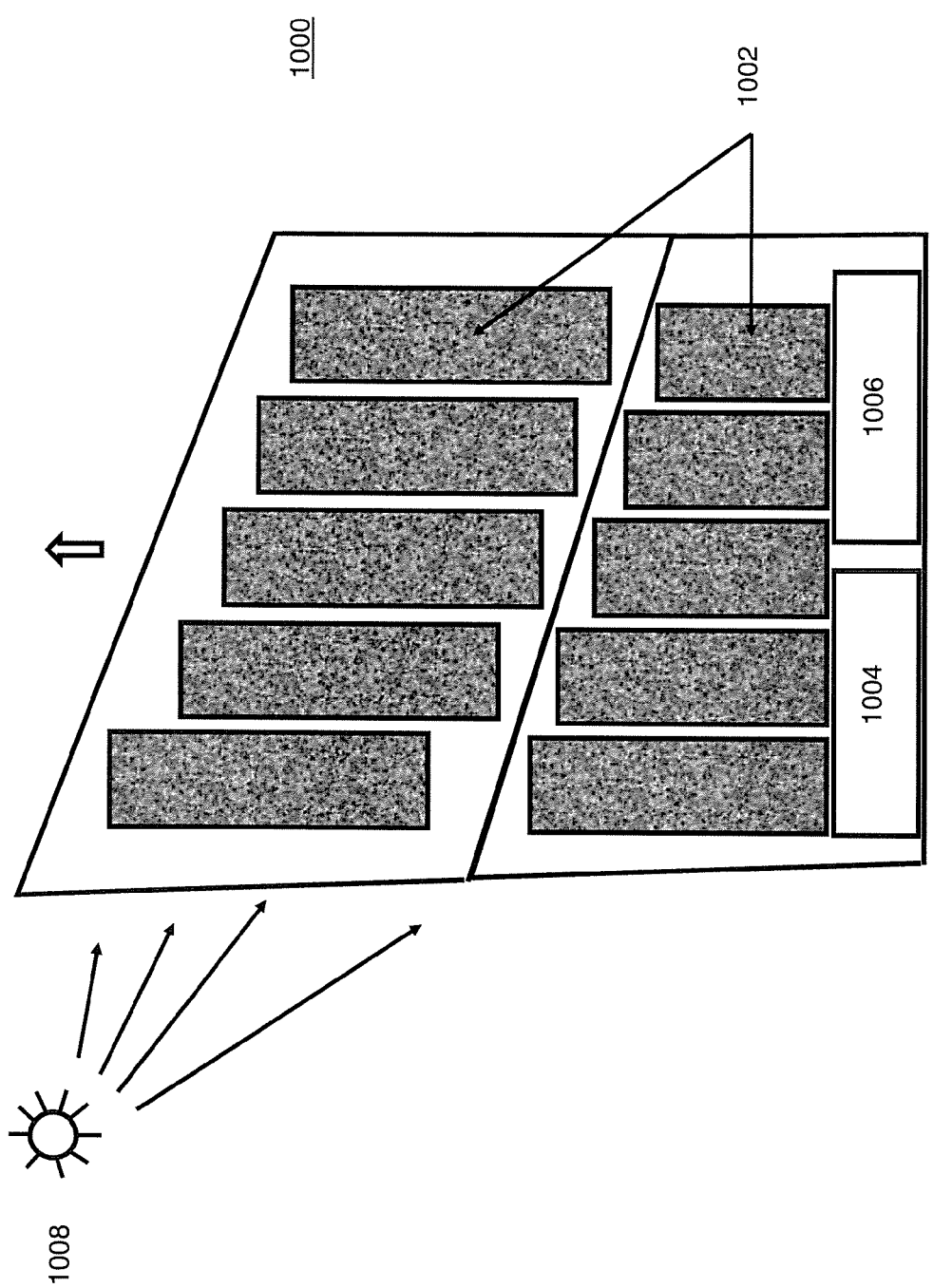
FIG. 10 is a schematic of a vegetation growth system in accordance with some embodiments.

Referring now to FIG. 10, in accordance with some embodiments, vertical growth mats 1002 may be arranged in a stacked configuration 1000 to further increase the effective growing area. In this example, the mats are arranged to receive light from a source 1008, and are co-located with an anaerobic digester 1004 and gas cleaning, liquefaction, and/or storage stage 1006. According to some embodiments, light source 1008 may be the sun or an artificial light source, such as a high efficiency red or blue LED. According to some embodiments, mats 1002 may be arranged on rollers as described with respect to FIG. 1 and system 100. Additionally, the position of mats 1002 may be variable according to the location of the sun, for instance, as described with respect to FIGS. 9A-9D.

Because the use of a vertical suspended growing mat may be used in conjunction with a uniformly flat vegetation such as grass, and a simple harvesting technique such as mowing, for example, it is possible to efficiently make use of the vertical volume above what would be the natural growing area available. The yield therefore increases exponentially for a given land area in accordance with some embodiments. As an example, the anaerobic digestion of cuttings taken from one hectare of lawn grass, (approximately two football fields) will produce approximately 12 thousand liters of liquid methane per annum. According to an embodiment, for a 50 meter high growing mat spaced at 1 meter intervals over the same area of land, the yield would be 1.2 million liters of methane, an increase of one hundredfold. This represents a significant development for the introduction of zero carbon methane and the corresponding carbon emissions.

Figure 11:
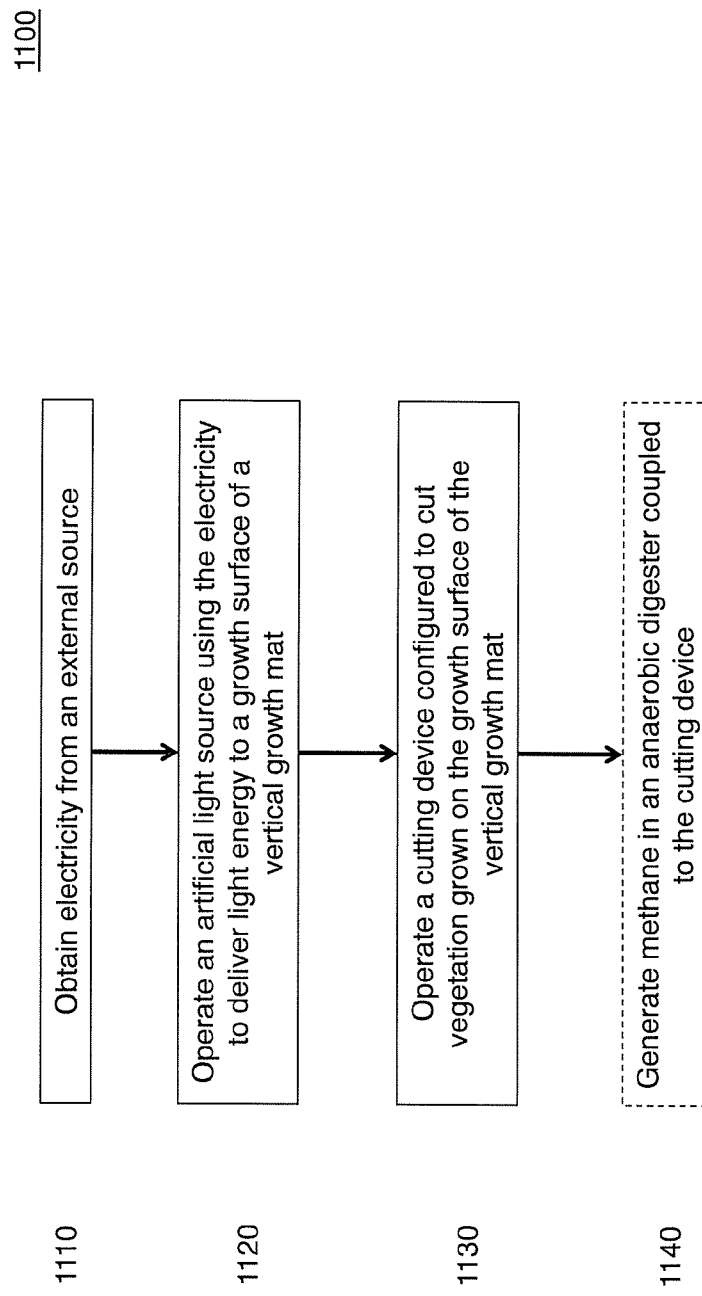
FIG. 11 is a flow chart of a vegetation growth process in accordance with some embodiments.

Referring now to FIG. 11, a process for growing vegetation 1100 is illustrated in accordance with some embodiments. Process 1100 may be performed, for instance, using systems 100, 300, and 400 of FIGS. 1, 3, and 4, respectively. Additionally, process 1100 may be performed using the stacked arrangement of mats illustrated in FIG. 10 and/or the offshore arrangement of FIG. 17.

Process 1100 may begin, for instance, with step 1110. In step 1110, electricity is obtained from an external source. The external source may be, for example, a renewable energy source such as one or more of wind, wave, solar, tidal and hydro-electric. The electricity may also be obtained from a mains electricity source. According to some embodiments, the electricity is obtained at a below-average cost due to one or more of time of day and season. In an offshore implementation, the electricity may be obtained from a source locally generating electricity at the offshore platform.

In step 1120, an artificial light source is operated using the electricity to deliver light energy to a growth surface of a vertical growth mat. According to some embodiments, the process 1100 may also include providing natural light as well. This may enable, for instance, continuous growth of the vegetation through the combination of natural and artificial light. In certain respects, for instance as illustrated in FIGS. 9A-9D, the position of the growth mats may be varied based on the position of the sun.

In some embodiments, the vertical growth mat is mounted on a plurality of rollers for rotatable movement. Further, mechanical energy released from the movement of the vertical growth mat can be captured and then used in the growth process. For example, the captured energy can be used for powering a cutting device (e.g., in step 1130), moving a roller, powering a conveyor belt, and/or powering a compressor.

In step 1130, a cutting device is operated. The cutting device can be configured to cut vegetation grown on the growth surface of the vertical growth mat.

In step 1140, an anaerobic digester coupled to the cutting device is used to generate methane. According to some embodiments, step 1140 is optional. The methane may be stored for subsequent use. Additionally, the process 1100 may also include delivering nutrients to the vertical growth mat. The nutrients could include by-products obtained from the anaerobic digester.

Figure 12:
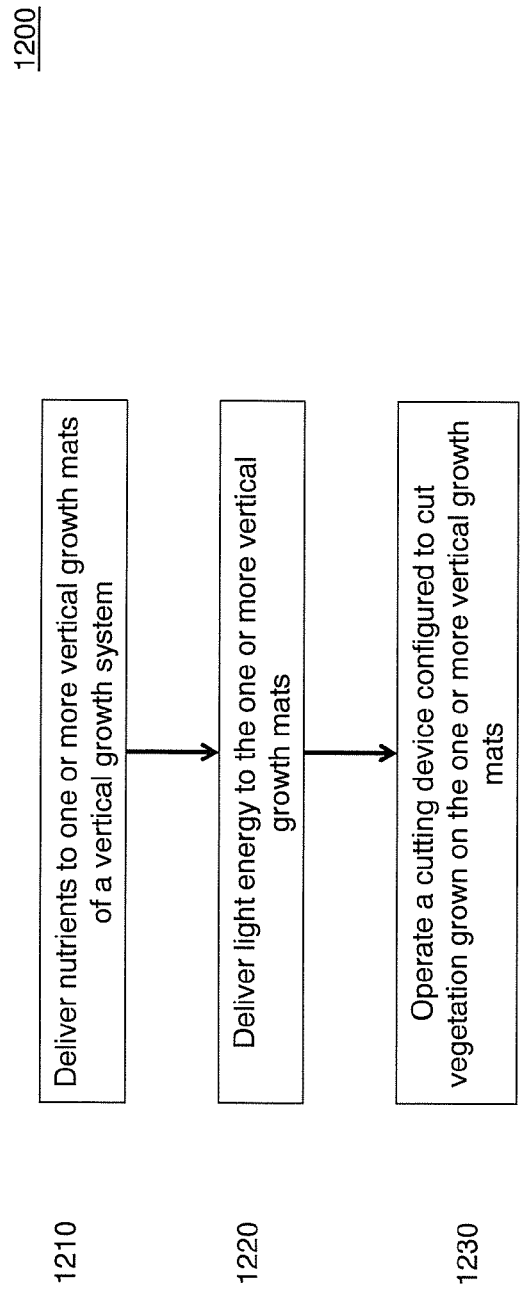
FIG. 12 is a flow chart of a vegetation growth process in accordance with some embodiments.

Referring now to FIG. 12, a process for growing vegetation 1200 is illustrated in accordance with some embodiments. Process 1200 may be performed, for instance, using systems 100, 300, and 400 of FIGS. 1, 3, and 4, respectively. Additionally, process 1200 may be performed using the stacked arrangement of mats illustrated in FIG. 10 and/or the offshore arrangement of FIG. 17.

Process 1200 may begin, for instance, with step 1210, in which nutrients are delivered to one or more vertical growth mats of a vertical growth system. The nutrients may include, for example one or more of fertilizer and or water. In step 1220, light energy is delivered to the one or more growth mats. In certain aspects, the light energy may be from an artificial and/or natural light source. In step 1230, a cutting device is operated to cut vegetation grown on the growth mats. According to some embodiments, at least one of the vertical growth mats of the system is suspended vertically on a roller. In certain aspects, the delivery of nutrients and/or delivery of light energy is performed such that a first mass of vegetation grown on a first side of the growth mat is greater than a second mass of vegetation grown on a second side of the growth mat. As a result, the first side falls downward and the second side moves upward.

Figure 13:
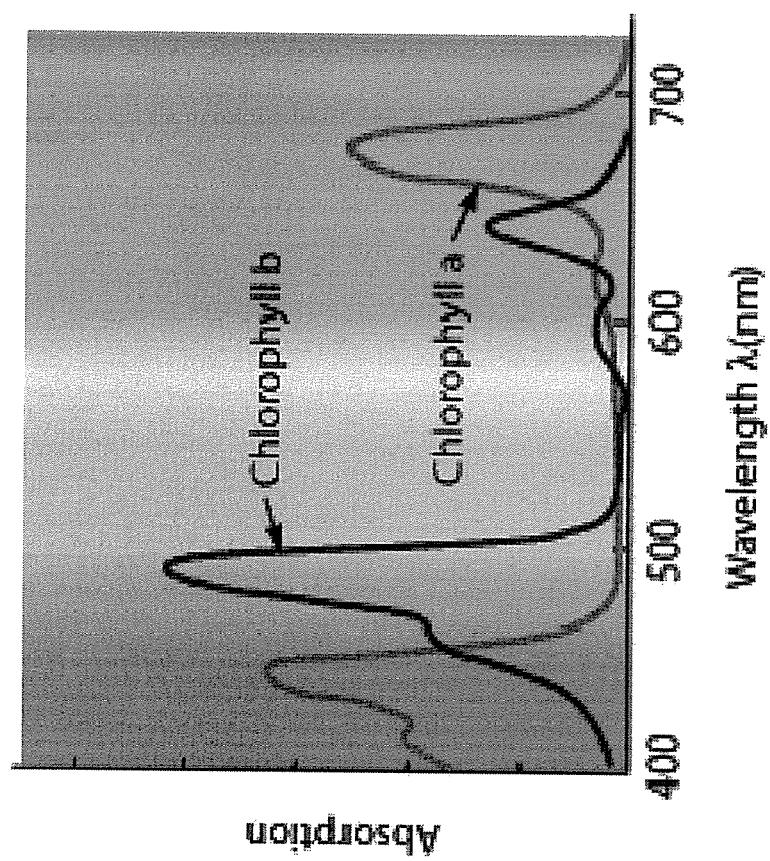
FIG. 13 is a data plot regarding absorption in accordance with some embodiments.
Figure 14:
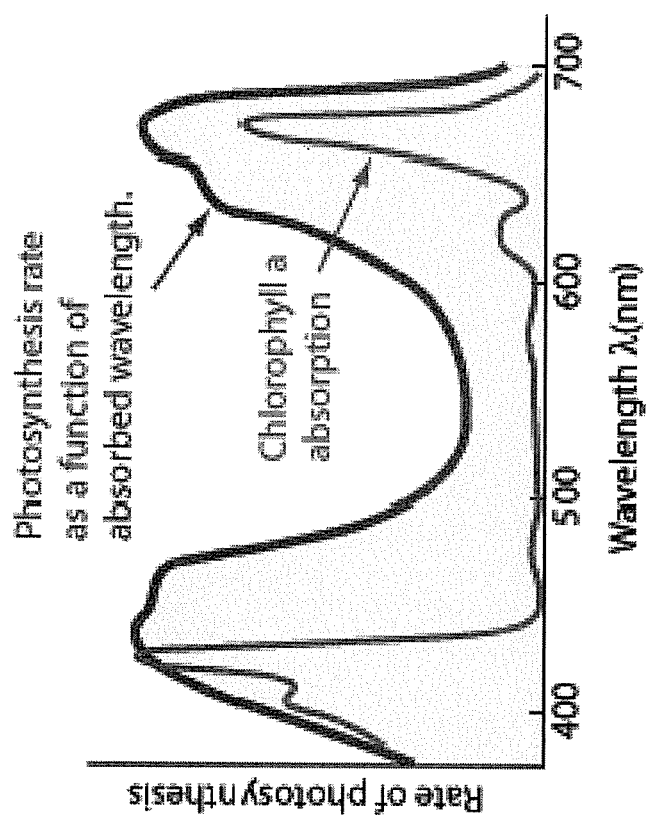
FIG. 14 is a data plot regarding photosynthesis in accordance with some embodiments.

The growth and processing of vegetation using the systems and methods of disclosed embodiment can have numerous advantages. For example, intermittent renewable energy sources often produce energy during the night time when energy requirements are low. Instead of switching off or dumping this electricity, it can be used to provide artificial light to allow a 24-hour growth period. This light could consist of the use of very efficient light emitting diode technologies centered at wavelengths in the red and blue part of the visible spectrum. This can increase the overall efficiency of the systems and processes disclosed herein. By way of illustration, optimum wavelengths for photosynthesis are shown in FIG. 13, where the absorption properties as a function of wavelength for chlorophyll types (a) and (b) are depicted. Additionally, the rate of photosynthesis is closely related to these optimum wavelengths as shown in FIG. 14. According to some embodiments, the waste heat from the light emitting diodes can be utilized to provide heat in colder climates in which to enhance the growth rates of the grass or other chosen feedstock.

Additionally, under natural conditions during the daytime, excess natural light can often result in slower vegetation growth. This may be, for instance, because the excess heat can restrict foliage's respiratory function. By using the spacing of a configuration in rows configured to provide the optimum spacing for the time of year and the latitude of the systems position relative to the Earth's equator and the Sun's elevation, the optimum natural light level can be achieved for most efficient growth depending on the intensity and angle of the Sun's illuminati relative to the vertical axis. According to some embodiments, the position of each row can be varied throughout the day to track the solar flux and increase efficiency.

By adopting an artificial growing process in accordance with some embodiments, it may be possible to achieve a photosynthetic efficiency that is much higher than that achieved in nature. For instance, the photosynthetic efficiency can be calculated as the energy capture and derived from the light absorption used in particular pathways to achieve the final result of synthesis of sugars. It is known that a total of 8 photons of light must be absorbed to reduce two molecules of NADP+. Operating in the Calvin cycle, the resulting two molecules of NADPH can produce one hexose molecule. The photon energy of a median energy photon at 600 nm is 2.07 eV, and for 8 moles of such photons the energy absorbed is $(8 \text{ moles})(6.022 \times 10^{23}/\text{mole})(2.07 \text{ eV})(1.6 \times 10^{-19} \text{ J/eV})/(4184 \text{ J/Kcal}) = 381$ Kcal. It takes 114 Kcal to reduce one mole of $CO_2$ to hexose, so the theoretical efficiency is 114/381 or 30%. Moore, R., Clark W. D., Kingsley, R. S., and Vodopich, D., Botany, Wm. C. Brown, 1995, report that 25% has been achieved under laboratory conditions. The top efficiency that they reported under natural growing conditions was the winter-evening primrose growing in Death Valley at 8%. Sugarcane has registered 7%, which is very important for a food crop. Sugarcane is a C4 plant, and under high sunlight conditions they will usually outperform C3 plants and others. The intensively cultivated agricultural plants average about 3% in photosynthetic efficiency, and most crops range from 1-4%. This is also typical of algae.

Some embodiments disclosed herein provide an exponentially scalable non-intermittent storable renewable energy source that can be positioned on either land or sea, but rely primarily on sunlight for its energy capture. In some embodiments, the generation of biogas, as well as production of methane and/or carbon dioxide, can be combined with the intermediary generation of liquid air from air extracted from the local environment using intermittent renewable energy sources such as wind, wave, solar, tidal and hydro. That is, according to some embodiments, the generation and use of liquid air from renewable sources can be combined with the subsequent cleaning and liquefaction of carbon dioxide and methane processes for converting energy.

Figure 15:
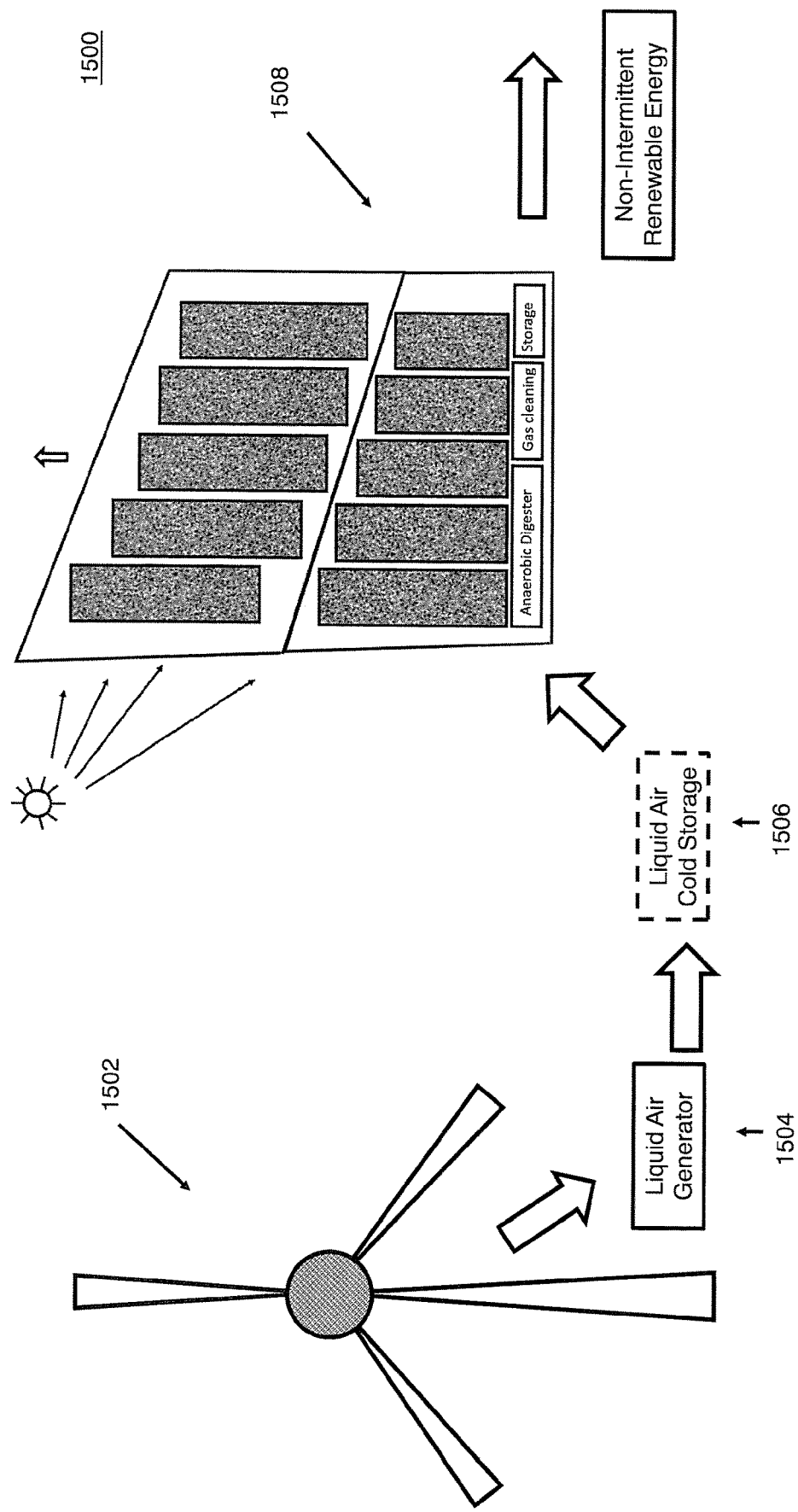
FIG. 15 is a diagram of a system incorporating renewable energy sources in accordance with some embodiments.

Referring now to FIG. 15, a process 1500 for the generation of energy is provided. The process 1500 may produce, for instance, non-intermittent renewable energy. The process 1500 shown in FIG. 15 may utilize a renewable power source 1502, which in some examples, does not need to be connected to any electricity or gas grid. In the example of FIG. 15, element 1502 is illustrated as a wind source, but it could be wave, solar, tidal and/or hydro in other examples. Additionally, a cryogenic generation system 1504 can be used to create a supply of liquid air extracted from the environment. The process 1500 may also optionally include storage of the liquid air, for instance in a cryogenic storage vessel for the liquid air 1506. The liquid air processing of 1502, 1504, and 1506 may be coupled to biogas generation and processing 1508. For example, they may be coupled to a system 100, 300,400, and/or 1000 as provided in FIGS. 1, 3, 4, and 10, respectively.

In in some embodiments, the cleaning of biogas, including for instance, as part of 1508, involves the separation of three primary constituents: Sulphur dioxide, carbon dioxide, and methane. In those embodiments, this can be most readily achieved using cryogenic processing such as the Linde distillation process. Once the gases have been separated through this process, e.g., the Linde process, the subsequent liquefaction process of the carbon dioxide and methane may be complicated by the explosive nature of methane. Liquefaction of a gas is most readily achieved through the compression, cooling and then rapid expansion of the gas, at which point it is cooled below its liquefaction temperature to form a liquid. However, this process requires electrical power to drive a compressor, and the compressor must be designed to be safe, which increases its cost and complexity.

In certain aspects, this process can be used to separate and subsequently liquefy firstly carbon dioxide and then methane due to their very different liquefaction temperatures of −37 C and −161 C, respectively. However, because of its explosive nature, the compression of methane typically requires expensive electro-mechanical equipment which is required to comply with strict safety guidelines such as ATEX. This makes the process both expensive and complicated, making the subsequent products comparable in price to existing fossil fuels. To remove the need for such equipment, embodiments disclosed herein may use the relatively safe and convenient properties of liquid air as an intermediary source of cold from which the liquefaction of methane and carbon diode can be achieved passively by passing the liquid air and methane and carbon dioxide mixture through either side of a heat exchanger.

Additionally, liquid air may be produced on an industrial scale anywhere on planet Earth through the use of well-known techniques such as the Linde process in its formation. Thus, and in some embodiments, it makes an ideal source of cold in remote areas, such as offshore in the ocean or in a desert. In certain aspects, all that is required is a mechanically driven compressor which can be driven by renewable sources. Also, unlike methane, liquid air is relatively inert and so the safety requirements for its distillation and liquefaction are straightforward. In certain aspects, as a liquid, it represents a convenient medium in which to store cold, which can be used for both the cryogenic milling and biogas cleaning, separation and liquefaction. For instance, it may be used—or a derivative, such as liquid nitrogen may be used—in connection with the cryogenic milling illustrated in FIG. 2. As its liquefaction requires the use of compressors, which if driven either mechanically directly or indirectly from electricity generated from intermittent renewable energy sources such as wind, hydro, solar, tidal and wave power it can be stored for long periods greatly in excess of the intermittency period. Also as a liquid, if required, the energy used to liquefy it can be partially recovered by allowing it to expand as it warms and using the pressure generated to drive a compressor in reverse to derive mechanical energy.

Because liquid air is so easily created, handled, and stored, and combined with the fact that it can be made from air anywhere on planet Earth and it exists as a liquid at a lower temperature (−195 C) than both methane and carbon dioxide, its use represents a convenient intermediary medium that can be used to first separate and then create both liquid methane and liquid carbon dioxide without the need for expensive explosion proof electro-mechanical equipment that would be used to handle methane. According to some embodiments, this can be achieved simply by passing firstly the carbon dioxide gas and then methane under gravity, over a simple heat exchanger through which cold liquid from the natural boil-off from the liquid air reservoir is flowing. This will cause both gases to condense into a liquid. This greatly simplifies and reduces the cost of both the separation and liquefaction of both carbon dioxide and methane.

With respect to a cryogenic milling process used to enhance the anaerobic digestion rate and yield, liquid air or one of its derivatives, liquid nitrogen provides a convenient supply of cold. For instance, as element 204 of FIG. 2. Additionally, and according to some embodiments, when generated from renewable sources in close vicinity to a vertical growth mat system, liquid air or one of its derivatives can remove the need for a supply of electricity or partial use of the resulting biogas for its production. This can result in a further reduction in production cost and/or increase in biomethane and carbon dioxide yield.

Figure 16:
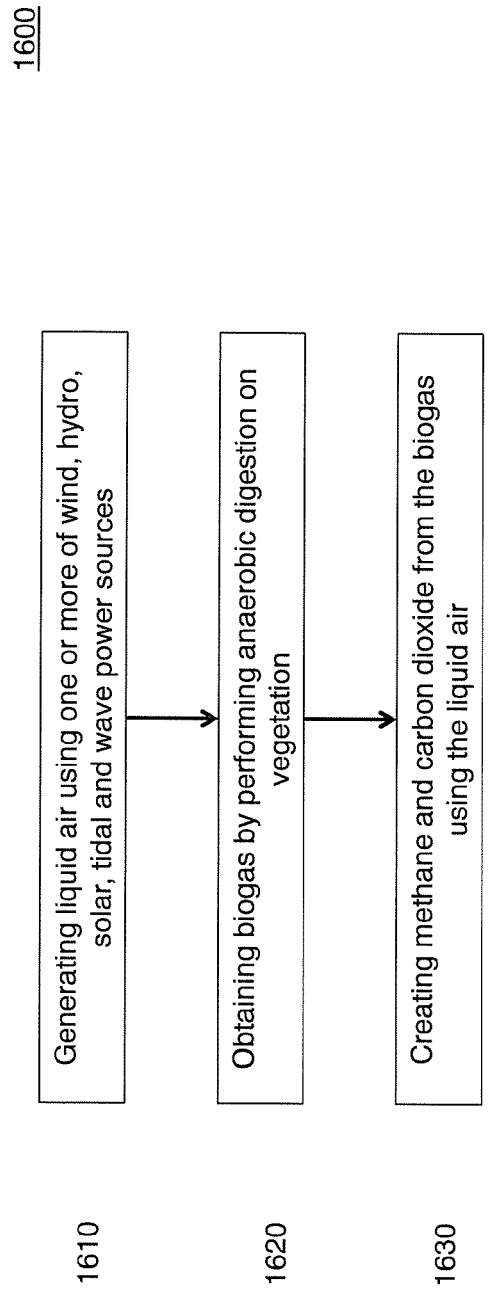
FIG. 16 is a flow chart of a biogas processing method in accordance with some embodiments.

Referring now to FIG. 16, a method 1600 for the processing of biogas is provided. The method may begin at step 1610, which includes generating liquid air. According to some embodiments, the liquid air can be generated by operating a mechanical compressor to compress and cool air. In certain aspects, the generation of the liquid air is performed using one or more of wind, hydro, solar, tidal, and/or wave power sources. These sources can directly power the process, or alternatively, generate electricity to power the process.

In step 1620, biogas is obtained. In some embodiments, obtaining the biogas includes performing anaerobic digestion. For instance, using one or more of systems 100, 300, 400, and/or 1000 as provided in FIGS. 1, 3, 4, and 10, respectively, biogas can be obtained by performing anaerobic digestion on vegetation obtained from a vertical growth mat.

In step 1630, carbon dioxide and methane are created from the biogas using the liquid air of step 1610. In some embodiments, this includes passing the liquid air and biogas through a heat exchanger to form liquid methane and liquid carbon dioxide. Additionally, the method 1600 can include operating a cryogenic milling device to disintegrate vegetation, where the milling device uses liquid air or a derivative of liquid air, such as liquid nitrogen.

Figure 17:
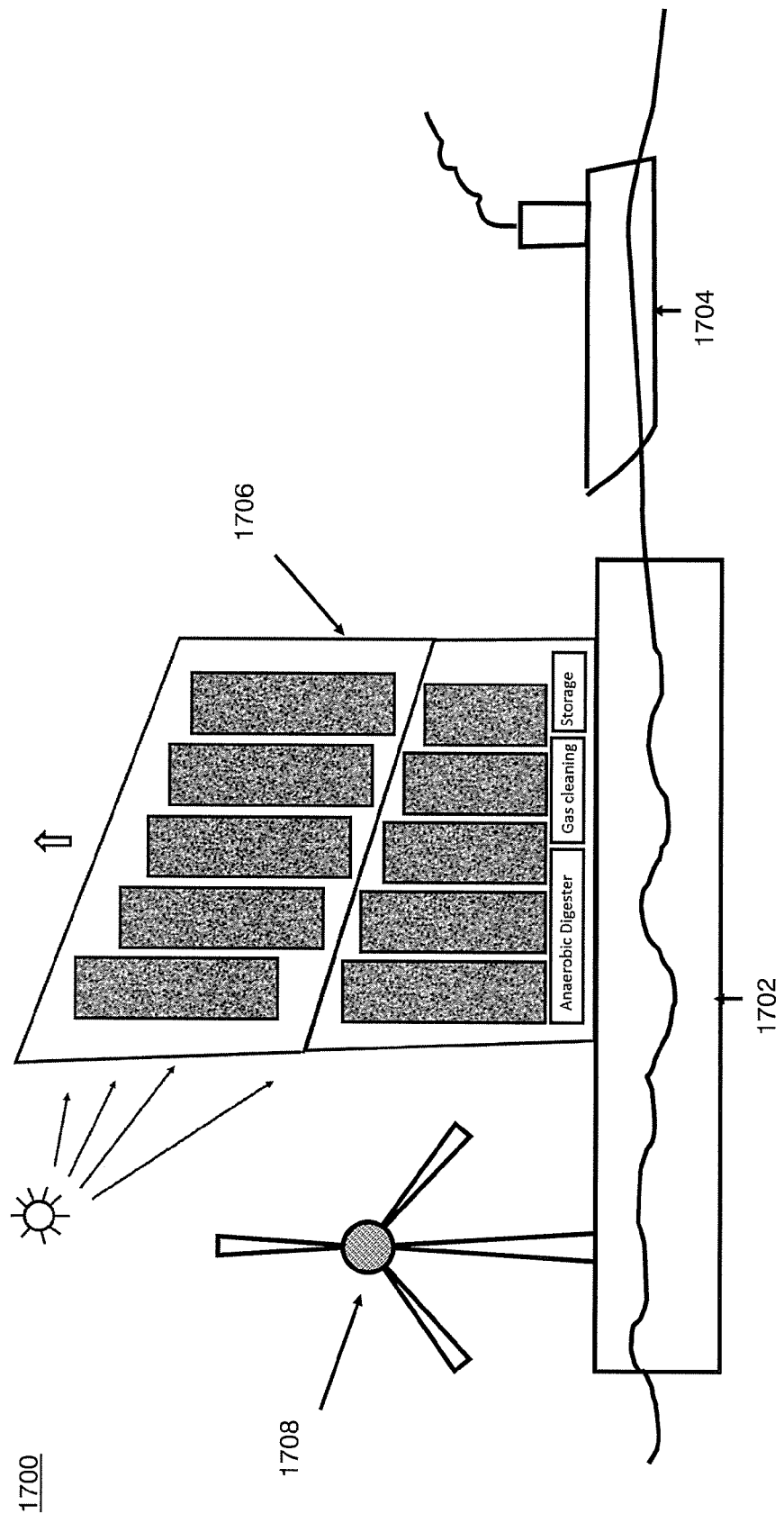
FIG. 17 is a diagram of an offshore system in accordance with some embodiments.

Referring now to FIG. 17, FIG. 17 illustrates an example 1700 of how embodiments may be implemented in an offshore platform 1702 with tanker 1704. For example, one or more systems 1706 for growing vegetation in accordance with disclosed embodiments, including systems illustrated in FIGS. 4 and 10, can be implemented on platform 1702. In certain aspects, an offshore location also has an advantage that it does not need to make use of land. For example, there may be no need for land rental or purchase, particularly if implemented in international waters.

Additionally, offshore implementation 1700 may also have an advantage over other offshore energy generation schemes in that there is no need to connect the system to any electrical grid or pipeline. For instance, the output of the system 1706 can be liquid biomethane, which has an energy density that is comparable to oil based fuels and can be removed from the system by fuel tanker 1704. Moreover, in some embodiments, offshore implementation can also make use of one or more materials and energy sources found in offshore locations, and particularly in international waters. This includes, for instance, air, sunlight, water (sea and rain), wind and waves. Implementation 1700 can be positioned far out to sea, e.g., in international waters, where there is minimal visual impact and there is potentially no need for government permissions. In certain aspects, it can also be moved if necessary during seasonal solar, rain, wind or wave fluctuations.

Offshore locations tend to be windier than land locations and may also have access to tidal and wave power. They may also be subject to relatively predictable daily or seasonal winds tides and swells emanating from lunar, geographical and solar conditions. For example, a platform 1702 positioned in an offshore location in the vicinity of an inland desert may be subject to strong alternating onshore and offshore winds caused by the diurnal heating and cooling of the desert relative to the constant temperature of the sea. These regular winds, which would otherwise be difficult to exploit due to the lack of electricity grid infrastructure usually occurring in such a remote location, can be captured via windmill 1708. Although a windmill is depicted in this example, other renewable sources may be used, such as solar, tidal, and hydro-electric electricity sources.

While various embodiments of the present disclosure are described herein, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

Additionally, while the processes described above and illustrated in the drawings are shown as a sequence of steps, this was done solely for the sake of illustration. Accordingly, it is contemplated that some steps may be added, some steps may be omitted, the order of the steps may be re-arranged, and some steps may be performed in parallel.

The invention claimed is:

1. A system for growing vegetation, comprising:
a rotating growth mat;
one or more rollers, wherein said rotating growth mat is suspended vertically from at least one of said rollers; and
a cutting device,
wherein said mat comprises a growth side and an inhibited side,
wherein said cutting device is configured to cut vegetation grown on said growth side of said rotating growth mat, and
wherein said one or more rollers are configured such that a mass of the mat on the growth side is greater than a mass on the inhibited side, and as a result, the growth side falls downward and the inhibited side moves upward.

2. The system of claim 1, further comprising:
a nutrients delivery device positioned adjacent to said growth side of said mat; and
an artificial light source.

3. The system of claim 2, wherein said artificial light source is a red or blue light emitting diode.

4. The system of claim 1, further comprising:
an anaerobic digestion system, wherein said anaerobic digestion system is configured to operate using vegetation grown on said rotating growth mat and processed by said cutting device.

5. The system of claim 1,
wherein said growth mat comprises a backing layer and a plurality of growing pockets containing seed-growing compost.

6. A system for growing vegetation, comprising:
a plurality of rollers;
one or more artificial light sources; and
a plurality of rotating growth mats,
wherein each of said plurality of rotating growth mats is suspended vertically from at least one of said plurality of rollers and comprises a growth side and an inhibited side,
wherein a first of said plurality of vertical growth mats is located above a second of said plurality of growth mats,
wherein said plurality of vertical growth mats are arranged in one or more rows and the position of said one or more rows is variable according to the position of the sun, and
wherein said plurality of rollers are configured such that, for each of said plurality of rotating growth mats, a mass of the mat on the growth side is greater than a mass on the inhibited side, and as a result, the growth side falls downward and the inhibited side moves upward.

7. The system of claim 6, further comprising:
one or more cutting devices; and
an anaerobic digestion system, wherein said anaerobic digestion system is configured to operate using vegetation grown on said plurality of rotating growth mats and processed by said cutting device.

8. A system for growing vegetation offshore, comprising:
a rotating growth mat, wherein said rotating growth mat is suspended vertically from at least one roller and comprises a growth side and an inhibited side;
a cutting device, wherein said cutting device is configured to cut vegetation grown on said growth side of said rotating growth mat;
an anaerobic digestion system configured to operate using said vegetation grown on said rotating growth mat and processed by said cutting device; and
an offshore platform, wherein said rotating growth mat, cutting device, and anaerobic digestion system are located on said offshore platform,
wherein said at least one roller is configured such that a mass of the mat on the growth side is greater than a mass on the inhibited side, and as a result, the growth side falls downward and the inhibited side moves upward.

9. The system of claim 8, further comprising:
one or more artificial light sources, where at least one of said one or more artificial light sources is powered by one or more of a wind, solar, tidal, and hydro-electric electricity source at said offshore platform.

10. The system of claim 1, wherein said cutting device is coupled to a cryogenic milling device configured to disintegrate said vegetation grown on said growth mat.

11. A system for growing vegetation, comprising:
a rotating growth mat;
one or more rollers, wherein said rotating growth mat is suspended vertically from at least one of said rollers; and
a cutting device,
wherein said mat comprises a growth side and an inhibited side,
wherein said cutting device is configured to cut vegetation grown on said growth side of said rotating growth mat, and
wherein said rotating growth mat is arranged such that mechanical energy is released as the mat rotates, and wherein the released energy is captured and used for at least one of powering the cutting device, moving at least one of said rollers, powering a conveyor belt, or powering a compressor.

* * * * *